US011338009B2

(12) United States Patent
Hakonarson et al.

(10) Patent No.: US 11,338,009 B2
(45) Date of Patent: May 24, 2022

(54) COMPOSITIONS AND METHODS FOR TREATMENT OF HEREDITARY CYSTATIN C AMYLOID ANGIOPATHY (HCCAA) AND OTHER NEURODEGENERATIVE DISORDER ASSOCIATED WITH ABERRANT AMYLOID DEPOSITS

(71) Applicant: The Children's Hospital of Philadelphia, Philadelphia, PA (US)

(72) Inventors: Hakon Hakonarson, Malvern, PA (US); Alvaro Gutierrez-Uzquiza, Madrid (ES); Michael March, Lansdowne, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

(21) Appl. No.: 16/789,923

(22) Filed: Feb. 13, 2020

(65) Prior Publication Data

US 2020/0323944 A1     Oct. 15, 2020

Related U.S. Application Data

(63) Continuation of application No. 16/124,798, filed on Sep. 7, 2018, now abandoned.

(60) Provisional application No. 62/555,496, filed on Sep. 7, 2017.

(51) Int. Cl.
*A61K 38/06* (2006.01)
*G01N 33/50* (2006.01)
*A61P 25/28* (2006.01)

(52) U.S. Cl.
CPC ............ *A61K 38/063* (2013.01); *A61P 25/28* (2018.01); *G01N 33/5023* (2013.01); *G01N 33/5032* (2013.01)

(58) Field of Classification Search
CPC .............................. A61K 38/063; A61P 25/28
See application file for complete search history.

(56) References Cited

U.S. PATENT DOCUMENTS

| 2003/0022243 A1 | 1/2003 | Kondejewski et al. |
| 2009/0143433 A1 | 6/2009 | Hendrix |
| 2018/0086817 A1* | 3/2018 | Postrel |

FOREIGN PATENT DOCUMENTS

| CA | 2 357 053 A1 | 3/2003 |
| EP | 1 774 972 A1 | 4/2007 |
| WO | 2007/134449 A1 | 11/2007 |
| WO | 2009/012571 A1 | 1/2009 |
| WO | 2011/149917 A1 | 12/2011 |
| WO | 2012/177997 A1 | 12/2012 |

OTHER PUBLICATIONS

Jackowski, British J. Neurosurgery 9 (1995): 303-317.*
International Search Report, search completed Nov. 16, 2018, issued in corresponding International Application No. PCT/US2018/049884, filing date Sep. 7, 2018.
Extended European Search Report, dated Mar. 25, 2021, issued in corresponding European Patent Application No. 18855099.0, filing date Sep. 7, 2018.
Shahidi, Siamak et al., "Influence of N-acetyl cysteine on beta-amyloid-induced Alzheimer's disease in a rat model: A behavioral and electrophysiological study," Brain Research Bulletin, vol. 131, May 1, 2017, pp. 142-149.
Östner, Gustav, "Molecular Mechanisms in Amyloid Disorders. Novel Treatment Options in Hereditary Amyloid Cystatin C," Division of Clinical Chemistry and Pharmacology, Faculty of Medicine, Lund University, Sep. 14, 2013.
"Clinical Trials Register EudraCT No. 2017-004776-56," Sep. 19, 2018, EU Clinical Trials Register, Retrieved from the Internet: URL:https://www.clinicaltrialsregister.eu/ctr-search/trial/2017-004776-56/IS [retrieved on Nov. 24, 2020].
Head, Elizabeth et al., "A Combination Cocktail Improves Spatial Attention in a Canine Model of Human Aging and Alzheimer's Disease," Journal of Alzheimer's Disease, vol. 32, No. 4, 2012, pp. 1029-1042.
Snorradottir, Asbjorg Osk et al., "Pathological changes in basement membranes and dermal connective tissue of skin from patients with hereditary cystatin C amyloid angiopathy," Laboratory Investigation, vol. 97, No. 4, Apr. 2017, pp. 383-394.
Hara, Y. et al., "Evaluation of the Neuroprotective Potential of N-Acetylcysteine for Prevention and Treatment of Cognitive Aging and Dementia," The Journal of Prevention of Alzheimer's Disease, vol. 4, No. 3, 2017, pp. 201-206.
Wang, Jun et al., "Grape-Derived Polyphenolics Prevent ABeta Oligomerization and Attenuate Cognitive Deterioration in a Mouse Model of Alzheimer's Disease," The Journal of Neuroscience, vol. 28, No. 25, Jun. 18, 2008, pp. 6388-6392.
Fu, Ai-Ling et al., "Protective Effect of N-Acetyl-L-Cysteine on Amyloid Beta-Peptide-Induced Learning and Memory Deficits in Mice," Brain Research, vol. 1109, No. 1, Sep. 13, 2006, DOI:10.1016/j.brainres.2006.06.042, Abstract only.
Wang, Rui et al., "N-Acetylcysteine Prevents 4-Hydroxynonenal- and Amyloid-beta-Induced Modification and Inactivation of Neprilysin in SH-SY5Y Cells," Journal of Alzheimer's Disease, vol. 19, No. 1, 2010, pp. 179-189.
Ágeirsson, Bjarni et al., "Hereditary cystatin C amyloid angiopathy: monitoring the presence of the Leu-68 -> Gln cystatin C variant in cerebrospinal fluids and monocyte cultures by MS," The Biochemical Journal, vol. 329, No. 3, Feb. 1, 1998, pp. 497-503.
Sweeney, Patrick et al., Protein misfolding in neurodegenerative diseases: implications and strategies, Translational Neurodegeneration, vol. 6, No. 6, 2017, pp. 1-13.

(Continued)

*Primary Examiner* — Robert C Hayes
(74) *Attorney, Agent, or Firm* — Kathleen D. Rigaut; Howson & Howson LLP

(57) ABSTRACT

Compositions and methods for the treatment of amyloid deposit diseases, e.g., hereditary cystatin C amyloid angiopathy and other neurodegenerative disorders, are disclosed.

9 Claims, 12 Drawing Sheets

Specification includes a Sequence Listing.

(56) References Cited

OTHER PUBLICATIONS

Abrahamson, Magnus et al., "Increased body temperature accelerates aggregation of the Leu-68 -> Gin mutant cystatin C, the amyloid-forming protein in hereditary cystatin C amyloid angiopathy", Proceedings of the National Academy of Sciences USA, vol. 91, Feb. 1994, pp. 1416-1420.

Bocock, Jeffrey P. et al., "Human proteoglycan testican-1 inhibits the lysosomal cysteine protease cathepsin L," European Journal of Biochemistry, vol. 270, 2003, pp. 4008-4015.

Giustarini, Daniela et al., "N-Acetylcysteine ethyl ester (NACET): A novel lipophilic cell-permeable cysteine derivative with an unusual pharmacokinetic feature and remarkable antioxidant potential," Biochemical Pharmacology, vol. 84, 2012, pp. 1522-1533.

Jackowski, Andre, "Neural injury repair: hope for the future as barriers to effective CNS regeneration become clearer," British Journal of Neurosurgery, vol. 9, 1995, pp. 303-317.

Konarkowska, Barbara et al., "Thiol reducing compounds prevent human amylin-evoked cytotoxicity," FEBS Journal, vol. 272, 2005, pp. 4949-4959.

Lee, Sooyeon et al., "Lysosomal Proteolysis Inhibition Selectively Disrupts Axonal Transport of Degradative Organelles and Causes an Alzheimer's-Like Axonal Dystrophy," The Journal of Neuroscience, vol. 31, No. 21, May 25, 2011, pp. 7817-7830.

Levy, Efrat et al., "Stroke in Icelandic Patients with Hereditary Amyloid Angiopathy is Related to a Mutation in the Cystatin C Gene, an Inhibitor of Cysteine Proteases," Journal of Experimental Medicine, vol. 169, May 1989, pp. 1771-1778.

Östner, Gustav et al., "High throughput testing of drug library substances and monoclonal antibodies for capacity to reduce formation of cystatin C dimers to identify candidates for treatment of hereditary cystatin C amyloid angiopathy," Scandinavian Journal of Clinical & Laboratory Investigation, vol. 71, 2011, pp. 676-682.

Palsdottir, Astridur et al., "A Drastic Reduction in the Life Span of Cystatin C L68Q Carriers Due to Life-Style Changes during the Last Two Centuries," PLoS Genetics, vol. 4, No. 6, e1000099, Jun. 2008, pp. 1-7.

Snorradottir, Asbjorg Osk et al., "Deposition of collagen IV and aggrecan in leptomeningeal arteries of hereditary brain haemorrhage with amyloidosis," Brain Research, vol. 1535, 2013, pp. 106-114.

Snorradottir, Asbjorg Osk et al., "Parenchymal cystatin C focal deposits and glial scar formation around brain arteries in Hereditary Cystatin C Amyloid Angiopathy," Brain Research, vol. 1622, 2015, pp. 149-162.

\* cited by examiner

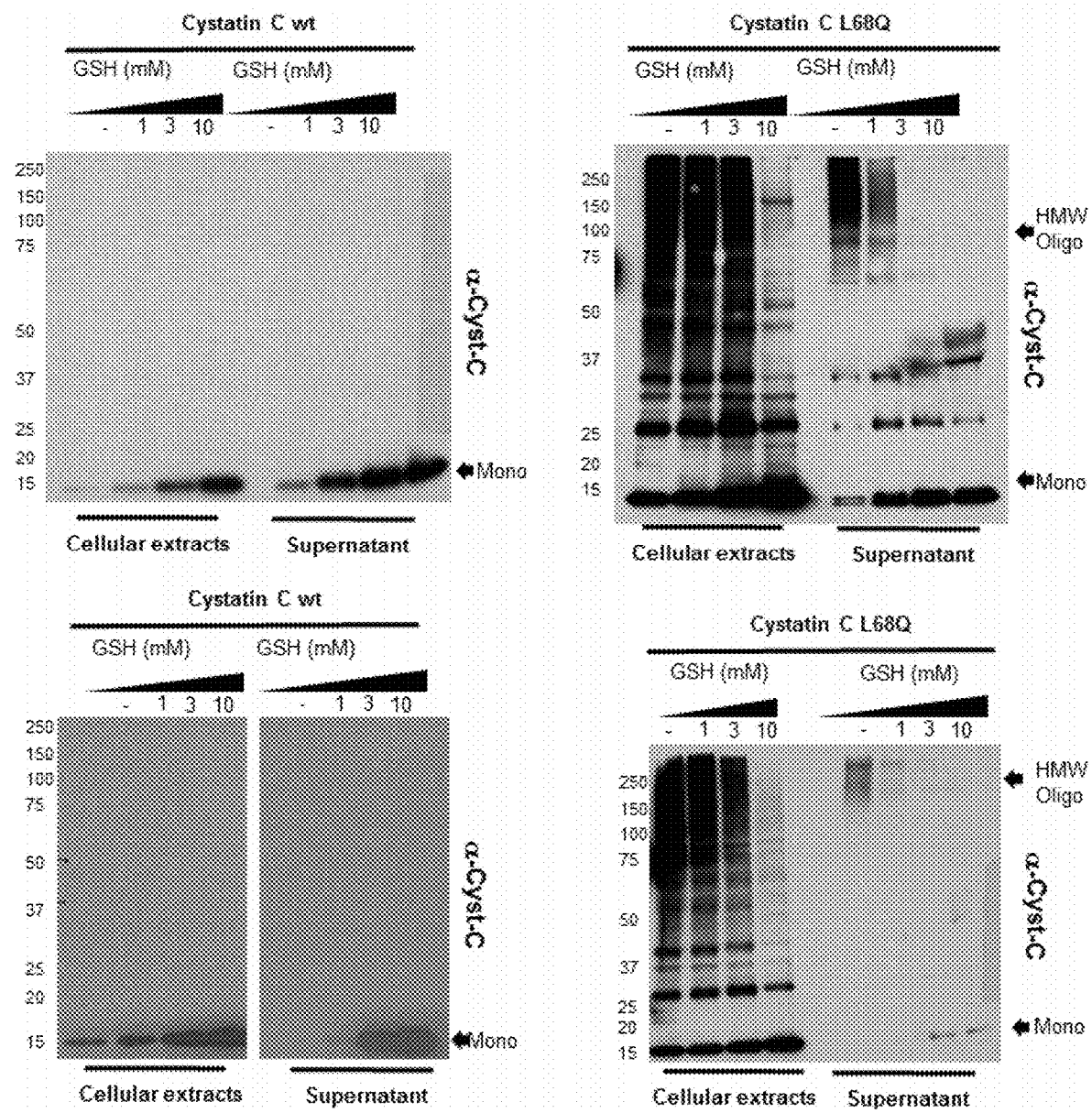
Fig. 1C (Biological replicates)

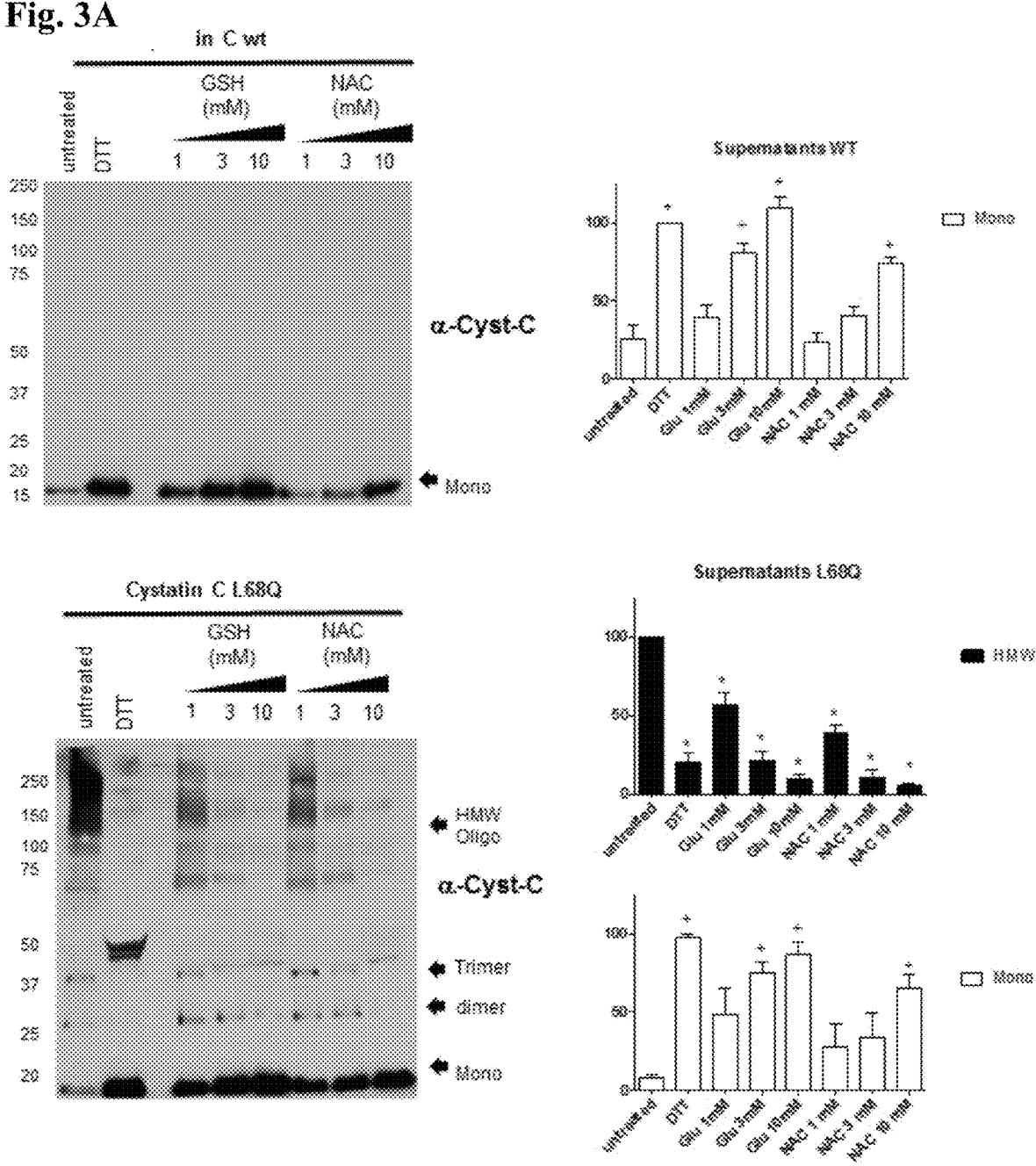

Figure 5

Reducing activity of GSH or NAC are critical for breaking oligomers into monomers of secreted Cystatin C L68Q NAC-A and NAC-M-E
impair olygomerization of intracellular and secreted Cystatin C L68

Fig. 8C  Cyst-C monomers are detectable at reduced levels in blood from subjects carrying the L68Q mutation. High molecular weight complexes were *potentially* detected in one carrier who is not taking NAC.

| Subject | CST3 Allele | NAC |
|---|---|---|
| Proband | L68Q | Taking |
| Sibling | L68Q | Taking |
| Mother | WT | Not taking |
| Father | L68Q | Taking |
| Relative | WT | Not taking |
| Child-1 | L68Q | Taking |
| Child-2 | WT | Not taking |
| Child-3 | Not tested | Not taking |
| Child-4 | Not tested | Not taking |

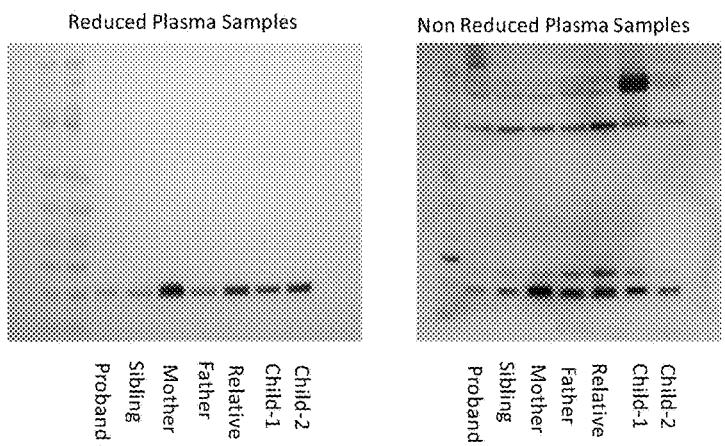

COMPOSITIONS AND METHODS FOR TREATMENT OF HEREDITARY CYSTATIN C AMYLOID ANGIOPATHY (HCCAA) AND OTHER NEURODEGENERATIVE DISORDER ASSOCIATED WITH ABERRANT AMYLOID DEPOSITS

CROSS-REFERENCE TO RELATED APPLICATIONS

The present application is a continuation of U.S. patent application Ser. No. 16/124,798, filed Sep. 7, 2018, which claims priority to U.S. Provisional Application No. 62/555,496 filed Sep. 7, 2017, the entire contents being incorporated herein by reference as though set forth in full.

INCORPORATION-BY-REFERENCE OF MATERIAL SUBMITTED IN ELECTRONIC FORM

Incorporated herein by reference in its entirety is the Sequence Listing submitted via EFS-Web as a text file named 6517US02_SequenceListing.txt, created Jun. 8, 2020 and having a size of 1,280 bytes.

FIELD OF THE INVENTION

The present invention relates to the fields of angiopathy, most notably including cerebral amyloid angiopathy and neurodegenerative disorders, associated with pathogenic fibril formation. More specifically the invention provides compositions and methods useful for the treatment and management of diseases associated with aberrant fibril formation, particularly hereditary cystatin C amyloid angiopathy (HCCAA) and Alzheimer's disease.

BACKGROUND OF THE INVENTION

Several publications and patent documents are cited through the specification in order to describe the state of the art to which this invention pertains. Each of these citations is incorporated herein by reference as though set forth in full.

Hereditary cystatin C amyloid angiopathy (HCCAA) is a dominantly inherited disease caused by a leucine 68 to glutamine variant of human cystatin C (hCC; L68Q-hCC).[1] HCCAA is classified as a cerebral amyloid angiopathy (CAA), a group of diseases in which amyloid deposits form on the walls of blood vessels in the central nervous system (CNS). Although HCCAA is rightly classified as a CAA disorder due to its strong cerebral presentation, hCC deposition is systemic and is also found in other internal organs. Most carriers of the mutation suffer micro-infarcts and brain hemorrhages in their twenties leading to paralysis, dementia and death in young adults, with an average life expectancy of 30 years.[2-6] Post-mortem studies in humans show that hCC is deposited in all brain areas, grey and white matter alike, most prominently in arteries and arterioles.

Human cystatin C, a cysteine protease inhibitor that belongs to the cystatin super-family, is a secretory type 2 cystatin, expressed in all nucleated human cells and found in all tissues and body fluids and at particularly high concentrations in cerebrospinal fluid.[2, 7-9] hCC inhibits cysteine proteases like papain and legumain by its interaction through multiple binding motifs resulting from the characteristic hCC fold.[9-11] Its normal conformation is composed of a polypeptide that folds into a five-stranded β-sheet, which partially wraps around a central α-helix. The N-terminal segment and two hair-pin loops build the edge of the protein, which binds into the active site of cysteine proteases and blocks their proteolytic activity.[12-14] The mutation of leucine 68 to glutamic acid destabilizes the packing between the beta sheets and the alpha helix, allowing the molecule to open. Two such open hCC molecules can interact with each other, with the helix of each molecule interacting with the beta sheet of the other; the resulting dimer is said to be the product of domain swapping.[15-17] Additionally, through a process called propagated domain swapping, long chains of molecules can be built, in which the free domain of each molecule interacts with a new hCC monomer.[18] The aggregation of proteins leads to the formation of highly ordered pathogenic fibrillar aggregates, called amyloid fibrils,[19, 20] which are implicated not only in HCCAA but also in a wide range of neurodegenerative diseases such as Alzheimer's, Parkinson's, Creutzfeldt-Jacob's, Huntington's disease and other CAAs.[20]

The degree of amyloid maturation observed in cystatin C deposits has been shown to vary between tissues (i.e, less prominent maturation in skin than in brain).[21] Although deposits in the skin are not comprised of amyloid fibers, quantitative studies on hCC deposition within the skin of mutant carriers showed that symptomatic carriers had significantly higher levels of hCC immunoreactivity in their skin than asymptomatic carriers. The fact that the quantity of hCC deposition in skin was associated with the progression of the disease in the CNS shows that skin biopsies could be used to assess disease progression and could, therefore, be of use in the evaluation of therapeutic interventions.[22]

Protein oligomers of different pathogenic amyloidogenic proteins precede the fibril formation stage in HCCAA and other diseases, although for HCCAA it is unclear if such oligomers lead directly to pathogenic fibrils, or if assembly of fibrils occurs most rapidly from monomers.[23] Drugs reducing aggregation of amyloid-producing proteins have the potential to reduce the formation of toxic oligomers known to occur in several types of amyloidosis.[24, 25] Previous investigations have suggested that preventing domain swapping of hCC might be used for treatment of HCCAA;[24] Nilsson and colleagues developed variants of WT hCC and L6Q-hCC with intra-chain stabilizing disulfide bonds preventing domain swapping that could form either dimers or amyloid fibrils.[26] These results suggest that the knowledge of the molecular mechanism causing the transition of physiologically normal and soluble proteins to toxic oligomers and insoluble fibrils is essential for the development of treatment strategies.

Östner et al. have previously attempted to prevent polymerization of hCC monomers, or disrupt or remove multimeric species, through various approaches.[24] As mentioned, modified, stabilized hCC monomers have been used to demonstrate that preventing domain swapping prevents aggregations. Antibodies can be raised specifically against the domain swapped, dimeric form of hCC; those antibodies were able to specifically remove dimers of hCC, and not monomers, from patient plasma using size exclusion chromatography.[27] A high-throughput screen of compounds has been pursued using the US Drug Collection (comprised of 1040 FDA approved compounds; (found on the world wide web at .msdiscovery.com/usdrug.html) in an effort to find molecules that prevent dimerization.[24] Although promising, this approach required large amounts of purified hCC protein produced in bacteria, and the compounds that were identified as inhibiting dimer formation were for the most part used at concentrations too high to be considered therapeutic in an organism.

Clearly, there is a need for improved methods and compositions for treating HCCAA.

SUMMARY OF THE INVENTION

In accordance with the present invention, a method for treating amyloid deposit disease comprising delivering an effective amount of at least one antioxidant to a patient, said antioxidant disrupting said amyloid deposit, thereby alleviating disease symptoms. Amyloid deposit diseases, include for example, hereditary cystatin C amyloid angiopathy (HCCAA), Alzheimer's disease, Parkinson's disease, Creutzfeldt-Jacob's disease, Huntington disease and other forms of cerebral amyloid angiopathies such as the Dutch form of the disease. In certain embodiments, the amyloid disease is HCCAA caused by mutated cystatin C. In other embodiments, the mutated cystatin C comprises a L68Q cystatin C. Preferred antioxidants for use in the method above, include, without limitation, glutathione, N-acetyl cysteine or a derivative thereof. In certain embodiments, the derivatives are selected from NAC-amide, NAC-ethyl ester and zinc mercaptide N-acetyl cysteine carboxylate salt.

In another aspect, a method for treatment of hereditary cystatin C amyloid angiopathy (HCCAA) in a human subject in need thereof is provided. An exemplary method comprises administration of an effective amount of N-acetyl cysteine or functional derivative thereof in a pharmaceutically acceptable carrier to the subject, the administration being effective to reduce amyloid-cystatin protein aggregates, thereby alleviating symptoms of HCCAA. In certain embodiments, the NAC derivative is selected from NAC-amide, NAC-ethyl ester and zinc mercaptide N-acetyl cysteine carboxylate salt. The method can optionally entail performing a skin biopsy on said subject following treatment to assess reduction in amyloid-cystatin protein aggregates in skin or measuring cystatin C monomer, dimer or oligomer in serum or plasma or the amount of monomer excreted in the urine.

In another aspect, the method can entail administration of additional agents which alleviate amyloid deposit symptoms. These include without limitation, one or more ionophores, one or more anti-inflammatory agents and one or more proteases. In other embodiments, siRNA directed to cystatin C coding sequences are administered to selectively block the mutated allele.

In another aspect of the invention, a method for treatment of a neurodegenerative disorder associated with pathogenic fibrillation protein aggregates in a human subject in need thereof is disclosed. An exemplary method comprising administration of an effective amount of N-acetyl cysteine or functional derivative thereof in a pharmaceutically acceptable carrier to the subject wherein the administration is effective to reduce said protein fibril aggregates, thereby alleviating symptoms of the neurodegenerative disorder. In certain embodiments, the disorder is selected from Alzheimer's disease, Parkinson's disease, Creutzfeldt-Jacob's disease, Huntington disease and other forms of cerebral amyloid angiopathy (CAA) such as the Dutch form.

In certain embodiments, the methods above comprise monitoring said patient for amyloid deposit levels.

In yet another aspect of the invention, a method for identifying therapeutic agents which alter amyloid-cystatin protein aggregate formation is provided. An exemplary method comprising providing cells expressing a nucleic acid encoding a mutant hCC protein, said mutant causing formation of amyloid-cystatin protein aggregates; and providing cells which express a hCC protein which lacks the hCC mutation. Both populations of cells are contacted with a test agent and assessed to determine whether the agent alters amyloid-cystatin protein aggregate formation of cells expressing the mutant relative to those expressing the wild type protein, thereby identifying agents which alter amyloid-cystatin protein aggregation. Agents so identified should have efficacy for the treatment of HCCAA or other disorders associated aberrant fibril formation.

Also provided is a pharmaceutical composition comprising an effective amount of an agent which acts as an antioxidant and, or a reducing agent for the treatment of amyloid deposit disease in a pharmaceutically acceptable carrier. Diseases to be treated with the composition, include for example, HCCAA, Alzheimer's disease, Parkinson's disease, Creutzfeldt-Jacob's disease, Huntington disease and other CAAs. In one embodiment, the agent is glutathione, N-acetyl cysteine or a derivative thereof. In a preferred embodiment, the agent is a derivative and is selected from NAC-amide, NAC-ethyl ester and zinc mercaptide N-acetyl cysteine carboxylate salt. The inventive compositions of the invention can also comprise one or more of an ionophore, an anti-inflammatory agent or a protease.

BRIEF DESCRIPTION OF THE DRAWINGS

FIG. 1A. Schematic representation of WT and L68Q mutant hCC proteins. Dashed line represents the N-terminal signal peptide subject to proteolysis. The red rectangle represents the Myc tag added to the C-terminal end. FIG. 1B: Incubation with glutathione impairs cystatin C di/oligomerization in cellular extracts and supernatants (biological replica) FIG. 1C. Biological replicates related to experiments shown in FIG. 2 where supernatants and cellular extracts were incubated in the presence of glutathione during 1 h at 37° C. with indicated concentrations. Samples were mixed with 2% SDS without reducing agents prior to electrophoresis, and proteins levels were detected by anti-cystatin C antibody WB.

FIG. 3A: Glutathione and N-acetylcysteine impairs oligomerization of secreted cystatin C L68Q. Supernatants were incubated in the presence of the indicated concentrations of glutathione or NAC for 1 h at 37° C. Samples were mixed with 2% SDS without reducing agents prior to electrophoresis, and protein levels were detected by anti-cystatin C antibody. The histogram represents the quantification by densitometry of the Western blot bands for the high molecular weight fraction (HMW) relative to the untreated sample or monomer (Mono) relative to the DTT treated sample. No HMW fraction was detected in supernatants from HEK-293T cells stably expressing hCC WT. (* significant at P<0.05 with respect to untreated (HMW); + significant at P<0.05 with respect to untreated (Monomer)).

FIG. 5. Reducing activity of GSH or NAC are critical for breaking oligomers into monomers of secreted Cystatin C L68Q. Supernatants were incubated in presence of oxidized (GSSG) or reduced glutathione (GSH), NAC or its inactive analogous (NAS) during 1 h at 37° C. with indicated concentrations. Samples were mixed with 2% SDS without reducing agents prior to electrophoresis, and proteins levels were detected by anti-cystatin C antibody.

FIGS. 8A-8C: Effects of NAC therapy in HCCAA patients. Cystatin C immunostaining (brown stain) was performed on 3 separate skin biopsies obtained from the same location of the back, from two members of a HCCAA family who are carriers of the hCC L68Q variant, using a rabbit-anti human cystatin C antibody. The biopsies in each left panel (skin biopsy 1 in FIG. 8A and FIG. 8B) were obtained when the family participated in research over 2 years prior to the initiation of this work. The biopsies in the middle figure panels (skin biopsy 2 in FIG. 8A and FIG. 8B) were obtained approximately 18 months later. The biopsies in the right panels (skin biopsies #3 in FIG. 8A and FIG. 8B) from both subjects show cystatin C protein complex deposition after 6 months of therapy with NAC. A marked reduction was seen in the proband (panel A) and the parent (panel B) after 6 months of NAC therapy. Panel A: Cystatin C immunostaining of skin biopsies from the proband. Panel B: Cystatin C immunostaining of skin biopsies from the parent. FIG. 8C. Cyst-C monomers are detectable at reduced levels in blood from subjects carrying the L68Q mutation. High molecular weight complexes appear to be present in one carrier who is not taking NAC.

DETAILED DESCRIPTION OF THE INVENTION

Figure 1A:
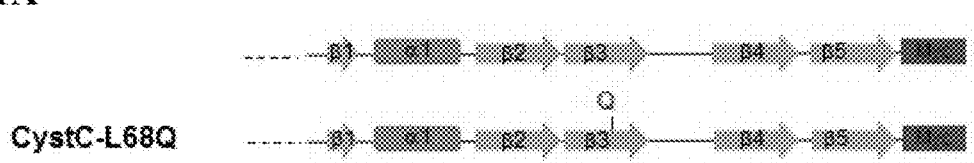
FIG. 1A: Genetically engineeredHEK-293T cells produce and secrete detectable levels of hCC (WT or L68Q) capable of oligomerizing under non-reducing conditions.

To create a system in which to test the ability of a compound to impact hCC multimerization while gaining some insight into its toxicity, we created cell lines that express high amounts of either wild type or mutant hCC. The cell lines and the monomeric and multimeric hCC that they create were characterized and employed in experiments for non-toxically interfering with aggregation of the mutant protein. Additionally, a biomarker study using NAC to treat human subjects with HCCAA was conducted.

This system facilitates evaluation of the ability of a molecule to interfere with aggregation of mutant hCC while also providing information about toxicity to cells or organisms. Clones of 293T cells that overexpress either wild type or mutant hCC were generated. These cells produce and secrete detectable levels of hCC. Importantly, we have established conditions that allow detection of high molecular complexes that form in both lysates and supernatants of cells expressing mutant hCC that are absent in cells expressing comparable amounts of the wild type protein. We are able to detect the high molecular weight complexes of mutant hCC by Western blotting under non-reducing conditions. Interestingly, a short incubation of either lysate or supernatant with one of two reducing agents, either reduced glutathione (GSH) or N-acetylcysteine (NAC), breaks oligomers of the mutant into monomers. Additionally, treatment of L68Q hCC expressing cells with either NAC or GSH reduces oligomerization of secreted hCC L68Q at 24, 48 and 72 h. Patients with HCCAA were subsequently treated with NAC for six months. As a biomarker of response, skin biopsies were obtained to determine if staining for amyloid cystatin C complexes were reduced in the skin following treatment. The proband, who was on the highest dose and had been on NAC for 9 months to treat mucous plugs in her lungs and had previously sustained 3 major strokes over a 9 month period prior to starting NAC, had approximately 75% reduction in the amyloid stain in the skin and has been event free for the 18 months of NAC therapy.

In summary, this study provides a new cellular model to test new therapies for the treatment of HCCAA and provides clear evidence that mutant hCC is a pharmacological target for reducing agents like NAC. Most importantly, the data implicate NAC as a potentially a useful therapy to treat this devastating disease based on skin biomarker results from three patients with HCCAA.

The following definitions are provided to aid in understanding the subject matter regarded as the invention.

In this invention, "a" or "an" means "at least one" or "one or more," etc., unless clearly indicated otherwise by context. The term "or" means "and/or" unless stated otherwise. In the case of a multiple-dependent claim, however, use of the term "or" refers to more than one preceding claim in the alternative only.

As used herein, "human cystatin C (hCC)" refers to a protein which functions as cysteine protease inhibitor that belongs to the cystatin superfamily. hCC is a secretory type 2 cystatin and is expressed in all nucleated human cells. L68Q-hcc refers to a mutated hCC wherein a leucine at position 68 is substituted for a glutamine variant.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of the hCC. Example agents include reducing agents such as NAC and derivatives thereof used alone and in combination. Other useful agents include, without limitation, glutathione, monensin, papain, cathepsin B, and falcipain. The biological activity of such agents can be assessed in the screening assays described herein below.

"Treatment," as used herein, covers any administration or application of a therapeutic for disease in a mammal, including a human, and includes inhibiting the disease or progression of the disease, inhibiting or slowing the disease or its progression, arresting its development, partially or fully relieving the disease, preventing the onset of the disease, or preventing a recurrence of symptoms of the disease. Example treatments include administration at least one NAC derivative at efficacious doses.

The terms "inhibition" or "inhibit" refer to a decrease or cessation of any event (such as fibril formation) or to a decrease or cessation of any phenotypic characteristic or the decrease or cessation in the incidence, degree, or likelihood of that characteristic. To "reduce" or "inhibit" is to decrease, reduce or arrest an activity, function, and/or amount as compared to a reference. It is not necessary that the inhibition or reduction be complete. For example, in certain embodiments, "reduce" or "inhibit" refers to the ability to cause an overall decrease of 20% or greater. In another embodiment, "reduce" or "inhibit" refers to the ability to cause an overall decrease of 50% or greater. In yet another embodiment, "reduce" or "inhibit" refers to the ability to cause an overall decrease of 75%, 85%, 90%, 95%, or greater.

The term "inhibitor" refers to an agent that slows down or prevents a particular chemical reaction, signaling pathway or other process, or that reduces the activity of a particular reactant, catalyst, or enzyme.

The terms "patient" and "subject" are used interchangeably to mean a mammal, including human.

N-acetyl cysteine (NAC)" is a derivative of cysteine that acts to reduce disulphide bonds associated with fibril formation present in neurodegenerative disorders such as HCCAA and Alzheimer's disease. While NAC and ester derivatives are exemplified herein, other NAC derivatives are known in the art and described in the following patent documents; U.S. Pat. Nos. 3,242,052, 3,591,686, 3,647,834, 3,749,770, 4,016,287, 4,132,803, 4,276,284, 4,331,648, 4,708,965, 4,711,780, 4,721,705, 4,724,239, 4,827,016, 4,859,653, 4,868,114, 4,876,283, DE150694C, EP0219455A2, EP0269017A2, EP0280606A1, EP0304017A2, and EP0339508A1 which are incorporated herein by reference.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction.

With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element. Exemplary vectors of the invention include without limitation, adenoviral-based vectors, adeno-associated viral vectors and retroviral vectors.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radioimmunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other manners, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

Methods and Uses for Treating HCCAA and Other Neurodegenerative Disorders

Encompassed herein are methods of treating HCCAA and other neurodegenerative disorders in a subject, comprising administering an effective amount of NAC or a functional derivative thereof. The term "treatment," as used herein, includes any administration or application of a therapeutic for a disease or disorder in a subject, and includes inhibiting the disease, arresting its development, relieving the symptoms of the disease, or preventing occurrence or reoccurrence of the disease or symptoms of the disease.

In some embodiments, the treatment methods comprise identifying or diagnosing a subject as having a genetic alteration in hCC causative of HCCAA, and administering a NAC or a functional derivative thereof to the identified or diagnosed subject. In other embodiments, the subject has a different disease associated with pathological fibril formation, including but not limited to Alzheimer's disease.

The total treatment dose or doses (when two or more targets are to be modulated) can be administered to a subject as a single dose or can be administered using a fractionated treatment protocol, in which multiple/separate doses are administered over a more prolonged period of time, for example, over the period of a day to allow administration of a daily dosage or over a longer period of time to administer a dose over a desired period of time. One skilled in the art would know that the amount of therapeutic agent required to obtain an effective dose in a subject depends on many factors, including the age, weight and general health of the subject, as well as the route of administration and the number of treatments to be administered. In view of these factors, the skilled artisan would adjust the particular dose so as to obtain an effective dose for treating an individual having HCCAA.

The effective dose of therapeutic agent(s) will depend on the mode of administration, and the weight of the individual being treated. The dosages described herein are generally those for an average adult but can be adjusted for the treatment of children. The dose will generally range from about 0.001 mg to about 1000 mg.

In an individual suffering from a more severe form of the disease, administration of therapeutic agents can be particularly useful when administered in combination, for example, with a conventional agent for treating such a disease. The skilled artisan would administer therapeutic agent(s), alone or in combination and would monitor the effectiveness of such treatment using routine methods such as neurological or pulmonary function determination, radiologicor immunologic assays, or, where indicated, histopathologic methods.

Administration of the pharmaceutical preparation is preferably in an "effective amount" this being sufficient to show benefit to the individual. This amount prevents, alleviates, abates, or otherwise reduces the severity of HCCAA symptoms in a patient. Treatment of patients having HCCAA with an efficacious amount of NAC or a functional derivative thereof may produce improvements in neurological function, respiratory function, tapering of concomitant medication usage, or increased survival.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

Pharmaceutical compositions that are useful in the methods of the invention may be administered systemically in parenteral, oral solid and liquid formulations, subcutaneously, intradermally, intramuscularly, sublingually, topically, intraperitoneal, nasally, percutaneous, respiratory, ophthalmic, suppository, aerosol, topical or other known routes of administration. In addition to the agent(s) useful for treating a HCCAA, the pharmaceutical compositions may contain pharmaceutically-acceptable carriers and other ingredients known to enhance and facilitate drug administration. Thus, such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to deliver/administer the appropriate agent to a patient according to the methods of the invention. The use of nanoparticles to deliver such agents, as well as cell membrane permeable peptide carriers that can be used are described in Crombez et al., Biochemical Society Transactions v35:p 44 (2007).

The pharmaceutical compositions can also comprise anti-inflammatory agents for co administration to further alleviate symptoms of amyloid disease. These include, without limitation, corticosteroids, aspirin, celecoxib, diclofenac, diflunisal, etodolac, ibuprofen, indomethacin, ketoprofen, ketorolac, nabumetone, naproxen, oxaprozin, piroxicam, salsalate, sulindac, tolmetin, interleukin (IL)-1 receptor antagonist, IL-4, IL-6, IL-10, IL-11, IL-13, cytokine receptors for IL-1, tumor necrosis factor-alpha, IL-18 and derivatives and biosimilars thereof.

The following materials and methods are provided to facilitate the practice of the present invention.

Cells and hCC WT vs. L68Q Variant Expression Constructs

Human embryonic kidney 293 (HEK-239T) cells were obtained from ATCC (Manassas, Va.) and grown at 37° C. in Dulbecco's modified Eagle's medium (DMEM) supplemented with 10% fetal bovine serum. A plasmid containing a cDNA of CST3 was obtained from Dharmacon (Lafayette, Colo.). The full length coding sequence was amplified with a c-terminal Myc tag by PCR using the forward primer GATCGAATTCGCCACCATGGCCGGGCCCCTGCGCG (SEQ ID NO: 1) and reverse primer TCGCGGCCGCCTA-CAGATCCTCTTCTGAGATGAGTTTTTGTTCGGCGT-CCTGACAGGTGGATTTCG (SEQ ID NO: 2) and ligated into the EcoRI and NotI sites of pBABE-CMV-Puro.[58] The L68Q mutation was introduced by QuikChange site-directed mutagenesis (Agilent, Santa Clara, Calif.) using primers: GTGAACTACTTCTTGGACGTCGAGCAGGGCCGAA-CCACGTGTACC (SEQ ID NO: 3) and GGTA-CACGTGGTTCGGCCCTGCTCGACGTCCAAGAAGT-AGTTCAC (SEQ ID NO: 4). All sequences were confirmed by Sanger sequencing. Wild type and mutant constructs were transfected into HEK-293T cells using Fugene HD (Promega, Madison, Wis.), with 3 µg DNA and 9 µl of the transfection reagent, according to the manufacturer's protocol. After transfection cells were incubated with fresh medium containing puromycin (1 µg/ml) for 3 weeks. After selection, stable clones of each transfectant were generated by limiting dilution. Clones were screened by Western blot using anti-hCystatin C antibody MAB1196 (R&D, Minneapolis, Minn.).

Western Blot

HEK-293T cells expressing hCC WT or the L68Q variant were washed twice with ice-cold phosphate-buffered saline (PBS) and lysed on ice using a freshly prepared ice-cold cell lysis buffer containing 50 mM Tris-HCl, pH 7.4, 100 mM NaCl, 50 mM β-glycerophosphate, 10% glycerol (w/v), 1% NP-40 (w/v), 1 mM EDTA, 2 mM $NaVO_4$, and a complete, EDTA-free, protein inhibitor cocktail (Roche Applied Science, Mannheim Germany) at 20 µl per mL of lysis buffer. After clearing the cell lysates by centrifugation (10 minutes, 21,000×g, 4° C.), the supernatants were collected and used for Western blotting. Sample buffer containing SDS, glycerol, Tris-HCl pH 6.8, and bromophenol blue was added to each sample to the following final concentrations: 2% SDS, 10% glycerol, 50 mM Tris-HCl, 0.02% bromophenol blue. In samples that were reduced, either DTT (50 mM final concentration) or β-mercaptoethanol (5% final concentration) were added. Equal volumes of lysate or supernatant samples were loaded on NuPAGE 4-12% Bis-Tris gels (Thermo Fisher Scientific, Waltham Mass.) without heating/boiling. Proteins were transferred to PVDF membranes (Millipore, Billerica, Mass.) and blotted with anti-hCystatin C, and developed by enhanced chemiluminescence (ECL; Thermo Fisher Scientific). ECL films were scanned, and densities of bands were determined using the gel analysis features of Fiji.[59]

Drug Treatments

HEK-239T cells were plated on 6-well plates and cultured for 2 days, at which point reduced glutathione (GSH) (Sigma, St. Louis, Mo.) or N-acetylcystein (NAC) (Sigma) were added to the indicated concentrations. Cells were incubated with compounds for 72 hours, and 100 µl samples of supernatants were removed at 24, 48, and 72 hours. Supernatants were cleared by centrifugation (10 minutes, 21,000×g, 4° C.). Sample buffer containing SDS, glycerol, Tris-HCl pH 6.8, and bromophenol blue was added to each sample to the following final concentrations: 2% SDS, 10% glycerol, 50 mM Tris-HCl, 0.02% bromophenol blue. When indicated, cells were washed with PBS and lysed and cystatin C levels were determined by means of Western blot analysis.

Statistical Analysis

The means and standard deviations of data were calculated. One-sided T-test tests were used to determine the level of significance with respect to the untreated samples, with $p<0.05$ being considered statistically significant.

Treatment of HCCAA Patients with NAC

Three 4 mm skin biopsies from the back were taken from each of the three studied individuals. The skin biopsies were formalin-fixed and paraffin-embedded. They were cut into 3 µm sections for immunohistochemistry and immunostained with rabbit polyclonal cystatin C antibody (Sigma, HPA013143) using the EnVision Detection System as previously described.[22] hCC immunoreactivity in the carriers skin biopsies was quantified by semi-automated image analysis using the ImageJ software as previously described.[22] Bright-field images of each section from the carriers were captured using a ×20/0.3 NA objective. RGB color images of the sections were imported to ImageJ. On each image, a rectangular 2000×2000 pixels region of interest (ROI) was defined. Subsequent processing yielding the % area coverage of hCC immunoreactivity within each ROI was performed as previously described[22]. The first biopsy was a historical biopsy taken approximately 2 years before the beginning of the study, during which the proband had experienced over 9 months of NAC therapy (400 mg 4× per day) to treat mucus plugging in the lungs following her third stroke. The second biopsy was taken immediately prior to the family-wide initiation of NAC treatment (600 mg of NAC 3× per day for 6 months). The third biopsy was taken following 6 months of 600 mg 3× per day of NAC therapy.

The proband received 400 mg NAC 4× per day for 9 months followed by 600 mg 3× per day for 6 months. The parent received only the 600 mg 3× per day for 6 months course. The proband never missed a dose; the parent did miss the middle dose 2-3 times per week.

Study Approval

All necessary permits for the use of skin biopsies from L68Q-CST3 carriers, and records associated with samples as well as medical information, were obtained from the National Bioethics Committee of Iceland, reference numbers 04-046-S2 and 15-060-S1. Both family members signed the informed consent. The NAC therapy was clinically and serendipitously prescribed as a mucolytic therapy to treat lung atelectasis in the proband. The other family member took NAC as a dietary supplement (i.e., purchasing NAC on-line through Amazon).

The following Examples are provided to illustrate certain embodiments of the invention. It is not intended to limit the invention in any way.

EXAMPLE I

As discussed above, HCCAA is a dominantly inherited disease caused by a leucine 68 to glutamine variant of Human Cystatin C (hCC; L68Q-hCC) (reference). Most carriers of the mutation suffer micro-infarcts and brain hemorrhages in their twenties leading to paralysis, dementia and death in young adults, with an average live expectancy of 30 years (1-5). Post-mortem studies in humans show that hCC was deposited in all brain areas, grey and white matter alike, most prominently in arteries and arterioles. These deposits are composed of amyloid fibers, consisting of hCC; this can be demonstrated through staining of post mortem tissue with Congo red staining which causes amyloid structures to show birefringence under polarized light (6).

To create a system in which to test the ability of a compound to impact hCC multimerization while gaining some insight into its toxicity, we created cell lines that express high amounts of either wild type or mutant hCC. This example describes our characterization of the cell lines and the monomeric and multimeric hCC that they create, attempts to non-toxically interfere with aggregation of the mutant protein as well as a pilot biomarker study using NAC to treat human subjects with HCCAA.

Genetically Engineered HEK-293T Cells Produce and Secrete hCC (wt or L68Q) Capable of Oligomerizing Under Non-Reducing Conditions.

In order to identify therapeutics agents capable of stopping the production of oligomers and fibrils of L68Q hCC, we generated genetically engineered HEK-293T cells with the expression of either wild type (WT) or L68Q mutant hCC. The protein was tagged at the c-terminus with a myc-tag; c-terminal tagging was chosen to avoid any interference with the cleavage of the signal peptide or secretion of the produced protein that may result from n-terminal tagging. After stable integration of these constructs into HEK-293T cells, we monitored both the secreted and the intracellular steady state levels of hCC WT and the L68Q variant. Analysis of hCC was developed by an SDS-PAGE gel electrophoresis system that allows the formation and detection of low- and high-molecular weight oligomer (LMW and HMW). As shown in FIG. 1A, cells produce and secrete detectable levels of both, hCC WT or the variant L68Q, capable of oligomerizing under non-reducing conditions (lanes #1 and 3). WT and L68Q expressing cells contain similar levels of hCC protein in lysates, indicating similar expression levels. However, conditioned supernatants from the L68Q expressing cells contain far less hCC protein than supernatants from the WT expressing cells. This indicates that the L68Q variant protein is not secreted from cells as effectively as the WT, consistent with previous reports (17, 18). While intracellular hCC WT exists predominantly as a monomer, with a small percentage of dimer (99 and 1%, respectively), intracellular hCC L68Q variant was found forming monomer, dimer but also LMW and HMW species as expected due to its increased propensity to form oligomers (19). Interestingly, the secreted form of hCC WT behaves similarly to the intracellular fraction, being found mainly as a monomer. In comparison, secreted hCC L68Q is found only as HMW. Remarkably, the oligomerization of both proteins, WT and L68Q variant, are completely abolished in presence of reducing agents DTT or b-mercaptoethanol; both are strong reducing agents that cause reduction of a typical disulfide bond.

Immunofluorescence assay was performed to detect the level of hCC protein in untransfected or WT and L68Q expressing 293T cells. hCC protein was mainly expressed in the cytoplasma. It shows a subcellular distribution consistent with the previously reported localization in late-endosomes/prelysosomes, as well as in the Golgi/ER/early-endosomal compartment, the latter in large agreement with typical characteristics of a secretory protein (20).

Figure 1B:
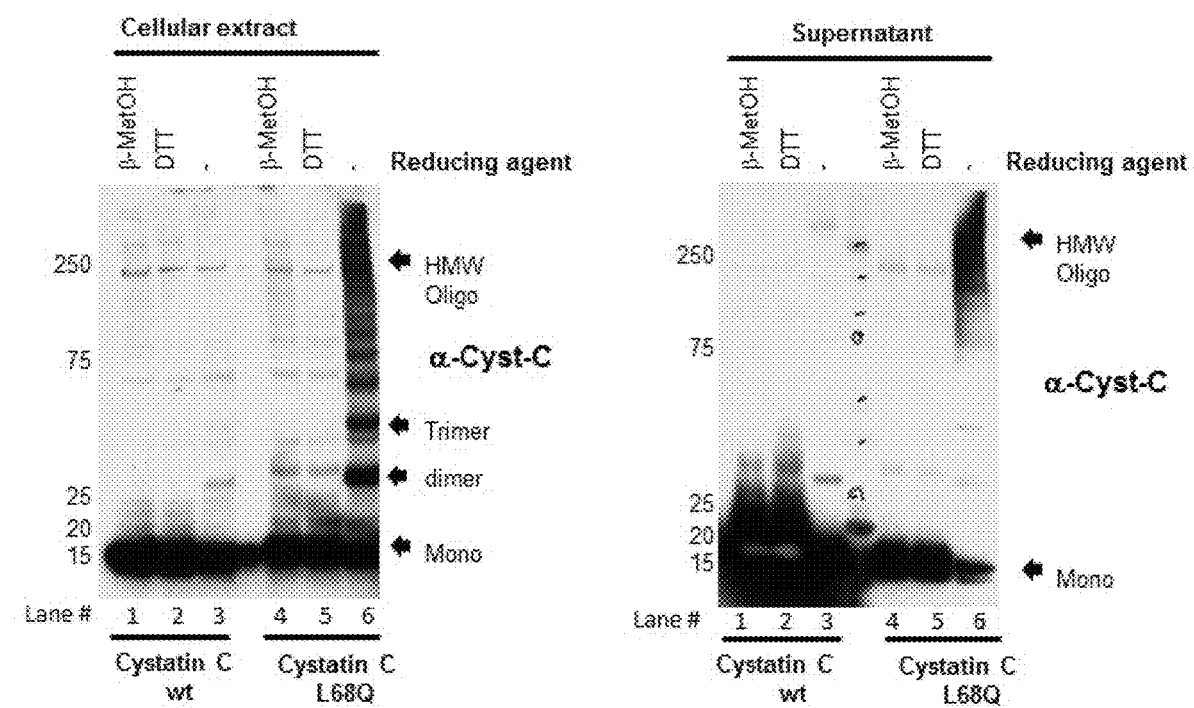
FIG. 1B. (left panel) Lysates from HEK-293T cells stably expressing hCC WT or L68Q mutant or supernatants (right panel) were mixed with 2% SDS with or without the reducing agents DTT or β-mercaptoetanol when indicated. Samples were subject to electrophoresis and CST3 levels examined by the Western blot procedure using anti-cystatin C antibody.
Figure 2A:
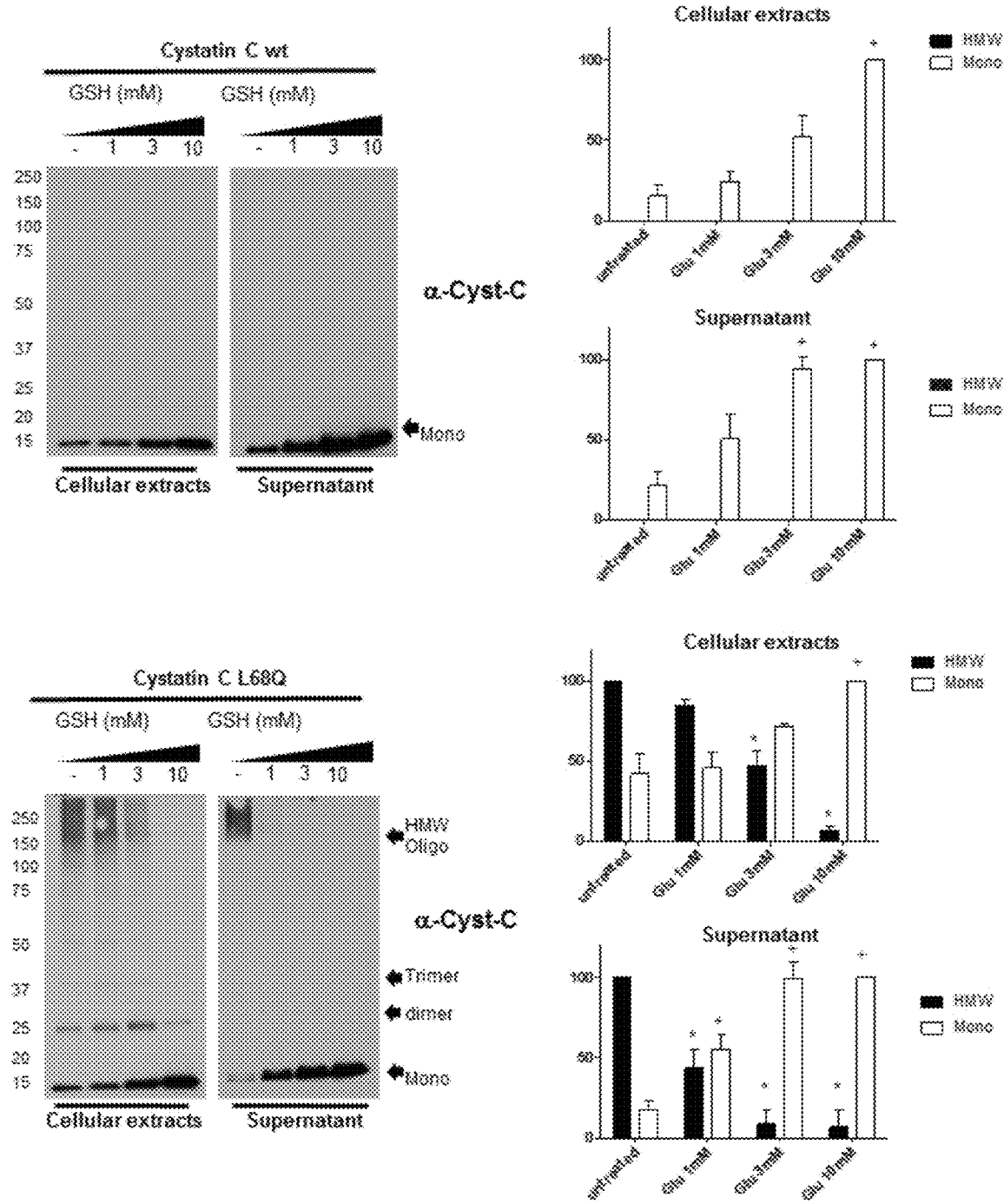
FIG. 2A: Incubation with glutathione impairs cystatin C di/oligomerization in cellular extracts and supernatants. Supernatants and cellular extracts were incubated in the presence of glutathione at the indicated concentrations for 1 h at 37° C. Samples were mixed with 2% SDS without reducing agents prior to electrophoresis, and protein levels were detected by Western blot for cystatin C. (N=3; * significant at $P<0.05$ with respect to untreated (HMW); + significant at $P<0.05$ with respect to untreated (monomer)).

Incubation with Glutathione Impairs hCC Di/Oligomerization in Cellular Extracts and Supernatants Depletion of LMW and HMW in presence of DTT or β-mercaptoetanol highlights the importance of disulfide bonds for the dimerization/oligomerization process; therefore we hypothesize that treatment with other reducing agents will impair the dimerization. We extensively characterized the effect of reducing agents on the dimerization/oligomerization levels of both the secreted and the intracellular levels of hCC WT and L68Q variant. Supernatants and cellular extracts were treated with different concentrations of GSH at 37° C. for 15 min. Notably, as FIG. 2A shows, treatments with 3 or 10 mM of GSH severely reduced the amount of dimer and/or HMW oligomer observed in both the secreted and the intracellular fraction of hCC WT or the L68Q variant. Quantitation of these results by densitometry shows that 3 mM of GSH displayed a ≈90% inhibition of the BMW in the secreted fraction and a ≈50% inhibition on the intracellular fraction of the L68Q hCC variant (FIG. 2A and FIG. 1B).

Incubation with NAC or Gluthathione Impairs Dimerization of Secreted hCC L680

Oxidized/reduced glutathione pair is critical to fight against oxidative stress, and, as shown in FIG. 2, it can effectively disrupt the dimers and HMW oligomers of hCC.

Figure 2B:
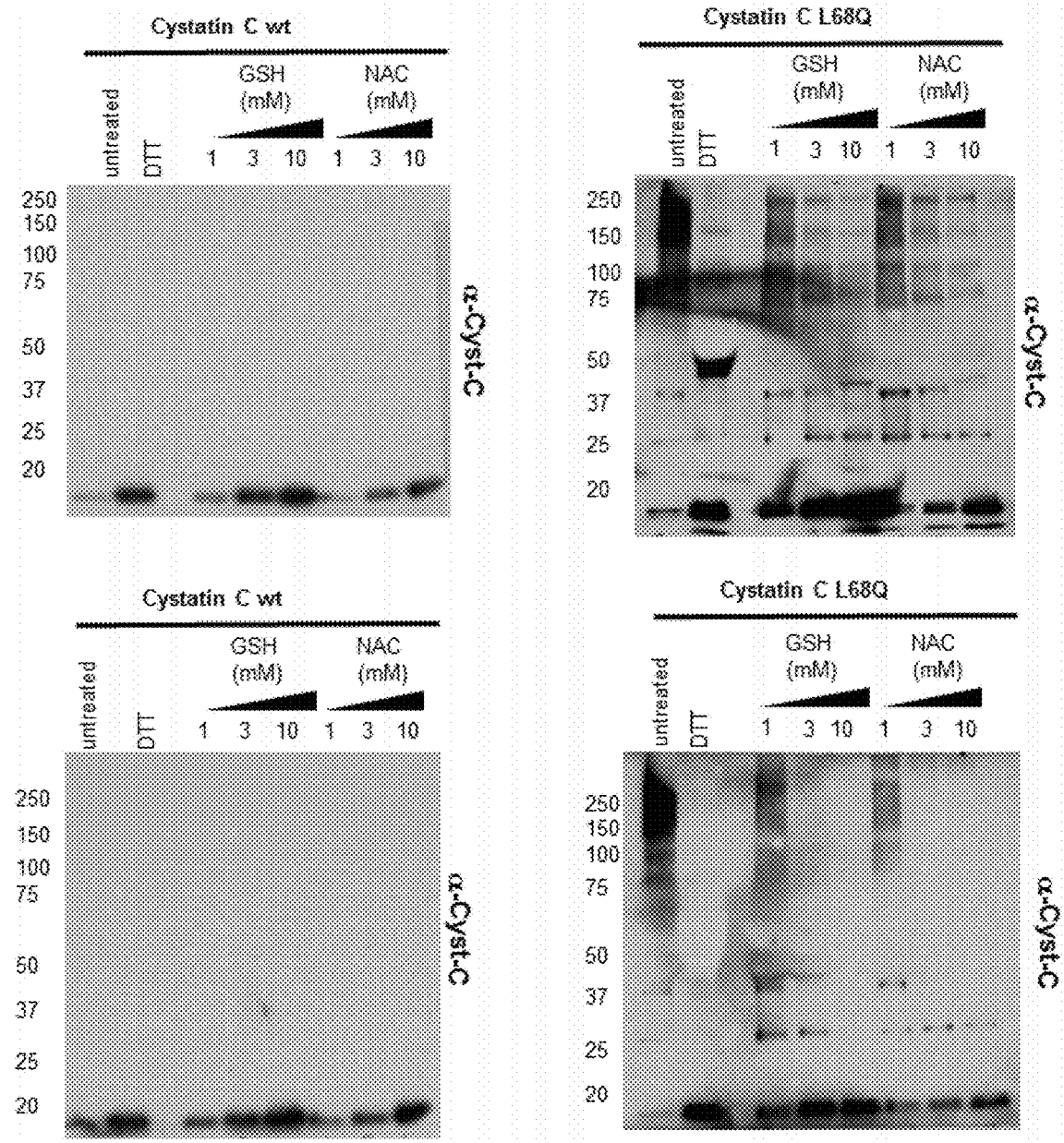
FIG. 2B: Glutathione and N-acetylcysteine impairs oligomerization of secreted cystatin C L68Q (Biological replicates). Biological replicates related to experiments shown in FIG. 3 where supernatants were incubated in the presence of glutathione or NAC during 1 h at 37° C. with indicated concentrations. Samples were mixed with 2% SDS without reducing agents prior to electrophoresis, and proteins levels were detected by anti-cystatin C antibody WB.
Figure 3B:
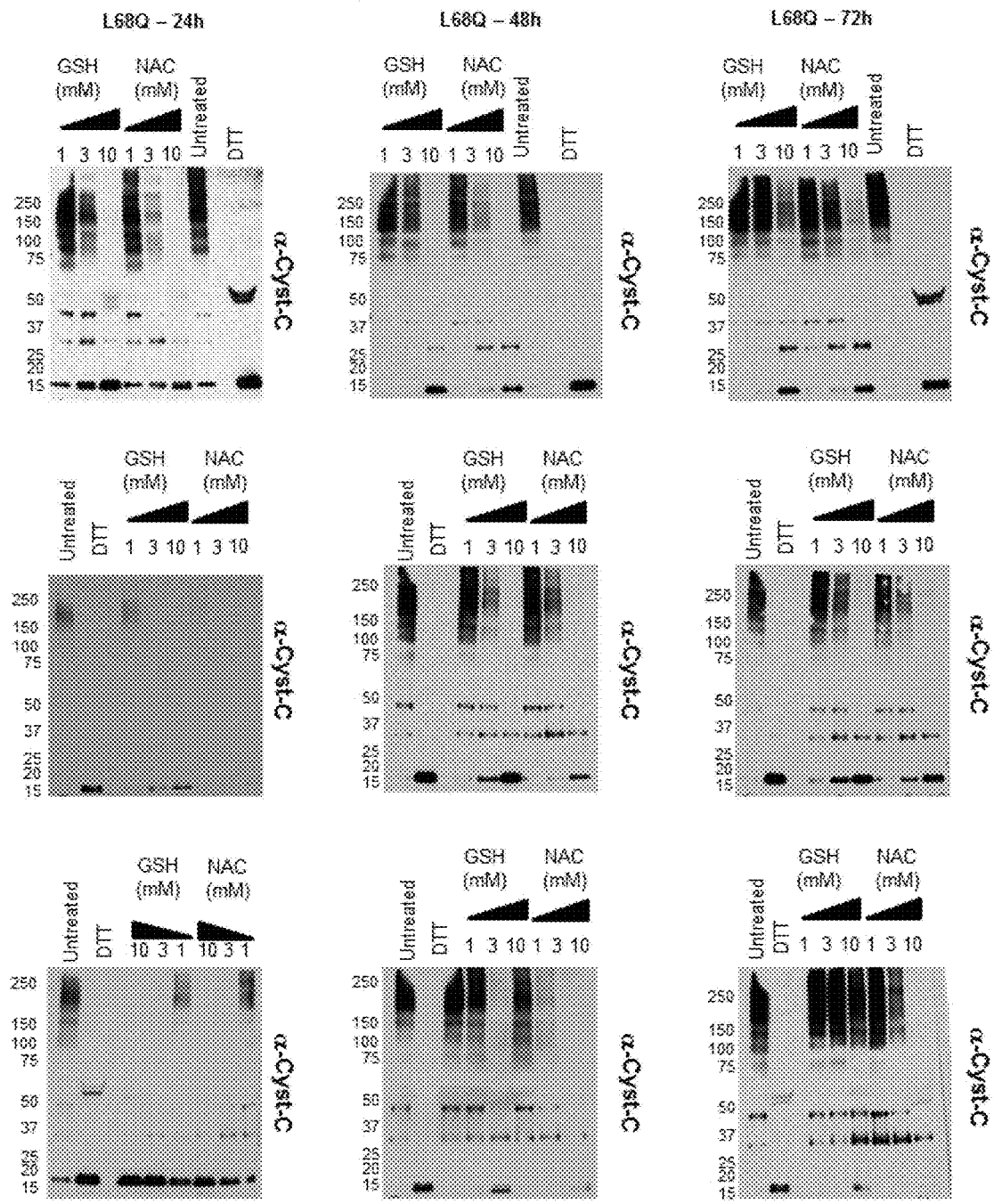
FIG. 3B: N-acetylcysteine impairs oligomerization of secreted cystatin C L68Q (Biological replicates) Biological replicates related to experiments shown in FIG. 4 where 293T cells expressing WT or L68Q cystatin C were incubated with the indicated amounts of compound during 24, 48 or 72 h. Small amounts of supernatant were removed from the cells and analyzed by Western blot at the indicated times. On days 2 and 3, only the L68Q supernatants were analyzed. Samples were mixed with 2% SDS without reducing agents prior to electrophoresis, and protein levels were detected by anti-cystatin C antibody WB.

Accordingly, we analyzed whether another reducing agent, the commonly used dietary supplement NAC (with similar antioxidant effects as GSH) would affect the oligomerization/dimerization of secreted hCC. Supernatants were treated with different concentrations of GSH and NAC at 37° C. for 60 min. As FIG. 3A shows, treatments with 3 or 10 mM of glutathione or NAC severely reduces the oligomerization/dimerization levels of secreted hCC L68Q variant in vitro. Quantitation showed almost complete ablation of HMW with 3 mM concentration of either GSH or NAC (FIG. 3A and FIG. 2B). This result clearly demonstrates that GSH or NAC are able to decrease the oligomerization levels of the pathogenic version of hCC L68Q and can be potentially used as for treatment of patients HCCAA.

Figure 4:
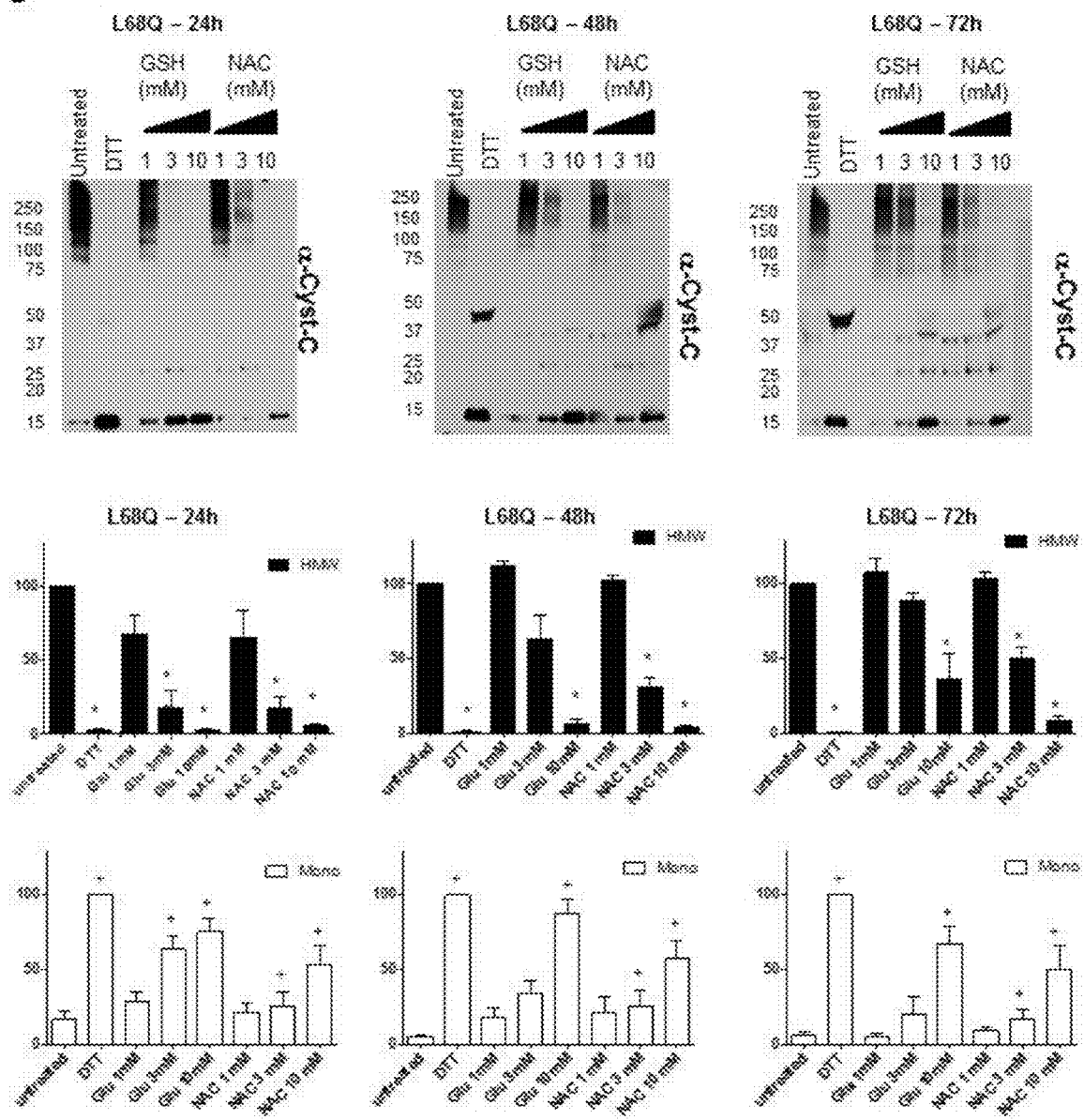
FIG. 4: NAC impairs oligomerization of secreted hCC L68Q. 293T cells expressing WT or L68Q cystatin C were incubated with media containing the indicated amount of either GSH or NAC for 24, 48 or 72 h. Small amounts of supernatant were removed from the cells and analyzed by Western blot at the indicated times. On days 2 and 3, only the supernatants from cells expressing hCC L68Q variant were analyzed. Samples were mixed with 2% SDS without reducing agents prior to electrophoresis, and protein levels were detected by anti-cystatin C antibody. The histogram represents the quantification by densitometry of the Western blot bands for the high molecular weight fraction (HMW) relative to the untreated sample or monomer (Mono) relative to the DTT treated sample. (* significant at P<0.05 with respect to untreated (HMW); + significant at P<0.05 with respect to untreated (Monomer)).

Presence of GSH or NAC Reduces Oligomerization of Secreted Cystatin C L68O at 24, 48 and 72 h To investigate whether the effect of NAC or GSH reduces the olygomerization of secreted hCC L68Q in a cellular system more reflective of in vivo biology, we treated cells expressing hCC WT or L68Q with both agents. Cells were seeded in plates and allowed to secrete hCC for 48 hours, at which point increasing concentrations of GSH or NAC were added to the cultures. Cells were cultured for 72 hours in the presence of reducing agents, with samples of the supernatants being removed after 24, 48, and 72 hours. Oligomerization status of hCC was determined by western blot at each time point. Cells were viable for the duration of the experiment in the presence of all concentrations (up to 10 mM) of both reducing agents. Proliferation of the cells was slightly impacted at the highest 10 mM concentration (data not shown). As shown in FIG. 4 (and FIG. 3B), treatment of cells with 10 mM of either GSH or NAC completely abolished the presence of HMW and LMW at 24 h and 48 h time points, and appreciable but incomplete reduction of HMW and LMW persisted at 72 h. Treatments with lower doses of NAC or GSH were only incompletely effective at 24 h and 48 h and no significant effect was detected after 72 h.

It is clear that treatment with reducing agents such as NAC or reduced glutathione of either supernatants or cellular extracts from cell lines engineered to overexpress the mutant version of human cystatin C (Cyst-C) reduces the formation of high molecular complexes of L68Q mutant Cyst-C. To determine if the effects of NAC and GSH are due to their capacity as reducing agents or some other properties of the compounds, supernatants and cell extracts were treated with compounds structurally similar to NAC and GSH that lack reducing activity. As shown in FIG. 5, treatment with either n-acetyl-serine (NAS), where the reducing sulfhydryl group in NAC is replaced with a hydroxyl group, or the oxidized form of glutathione (GSSH), does not affect high molecular weight complexes of L68Q Cyst-C, while significant reduction was observed with both reducing agents. The reducing activity of either NAC or GSH is required for the effects on Cyst-C oligomerization.

Figure 6:
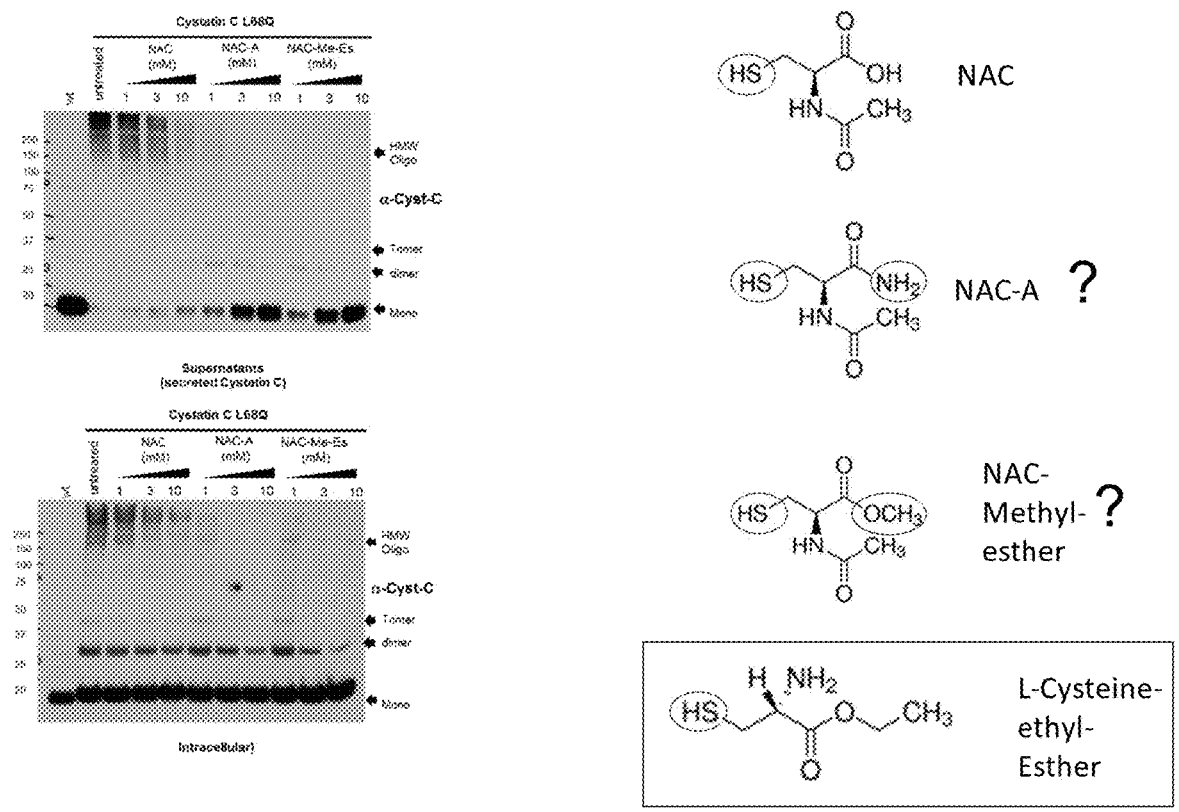
FIG. 6. NAC-amide and NAC-ethyl-ester impair oligomerization of intracellular and secreted Cystatin C L68. Supernatants and cellular extracts were incubated in presence of NAC, NAC-amide and NAC-methyl ester during 1 h at 37 C with indicated concentrations. Samples were mixed with 2% SDS without reducing agents prior to electrophoresis, and proteins levels were detected by anti-cystatin C antibody.

Multiple derivatives of NAC exhibiting improved reducing activity and bioavailability, as well as the ability to cross the blood/brain barrier have been generated. Two NAC derivatives have been tested with our cell culture system. As shown in FIG. 6, both an amide- and a methyl-ester derivative of NAC retain the ability to disrupt high molecular weight complexes of L68Q Cyst-C, when either supernatants or cell extracts are treated in vitro. Our data also indicate that both derivatives may be slightly more potent in their ability to disrupt oligomerization, as loss of high molecular signal was observed at 1 mM of the derivatives equivalent to that seen with 10 mM of NAC.

Figure 7:
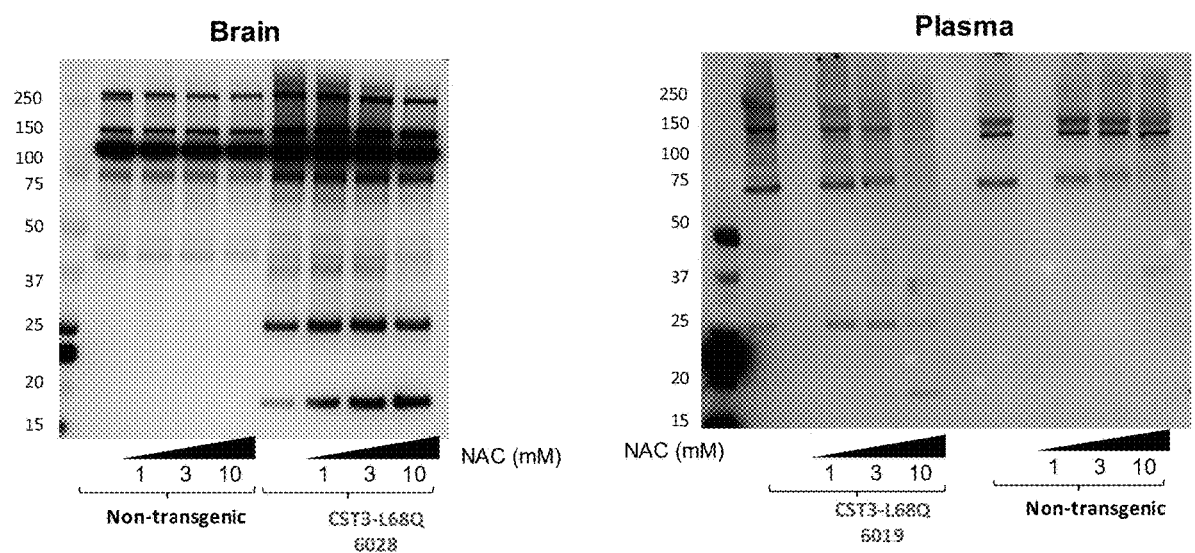
FIG. 7. High molecular weight complexes of Cyst-C L68Q can be detected in transgenic mice. Short incubation of NAC impairs oligomerization of Cyst-C L68Q on blood and brain extracts. Plasma or brain extracts were incubated in presence of NAC during 1 h at 37° C. with indicated concentrations. Samples were mixed with 2% SDS without reducing agents prior to electrophoresis, and proteins levels were detected by biotinylated anti-cystatin C antibody followed by streptavidin-HRP.

Additional results have been generated from transgenic mice that were obtained from our collaborator Eufrat Levy at New York University. These mice have been transformed with a human genomic DNA which contains the coding sequence of Cyst-C, while lacking non-coding portions of the gene which may impact expression levels. The mice do not display a phenotype comparable to that of HCCAA. However, we as shown in FIG. 7, we have been able to show the presence of high molecular weight Cyst-C complexes in both brain and blood of transgenic animals. Western blots from the mouse tissue extracts are not as clean as blots from the cell system, as the antibody we use to detect was raised in a mouse. Despite this complication, comparison of the transgenic mice (numbers 6028 and 6019) to the non-transgenic C57B16 animal shows considerable signal caused by the transgenic human Cyst-C. Although there are several non-specific high molecular weight bands observed in the non-transgenic samples, a clear high molecular weight "smear" is seen in the transgenic animals, consistent with what we observe in supernatant from the cell culture system. Treatment with NAC reduces this smear, and causes the appearance of monomer, showing that NAC is capable of reducing oligomerization in biological samples.

Effects of NAC Therapy in HCCAA Patients

There are several hundred patients in Iceland who suffer from HCCAA (i.e., suffering major strokes in their early 20's) and they all result from a founder mutation from the early 1500s. We have performed RNAseq on 30 subjects from 3 multiplex families and shown that genes involved in coronary disease, stroke and atherosclerosis are upregulated in mutation carriers of Cystatin C. As there is no therapy available for these patients, intervention that has a potential to delay or reverse the disease process would be readily approved by the Icelandic Medicinal Agency. Amyloid fiber dimerization is a critical step in the amyloid deposition process into small-medium sized brain arteries. In cell-based assays, we have shown that both the wild type and mutated proteins are expressed and that expression of the mutated protein dimerizes, a process that can be inhibited. Thus, drugs that block dimerization of the amyloid fibers would be anticipated to be effective in preventing amyloid deposition and halt progression of the disease process, thereby presenting an effective therapy.

Figure 8A:
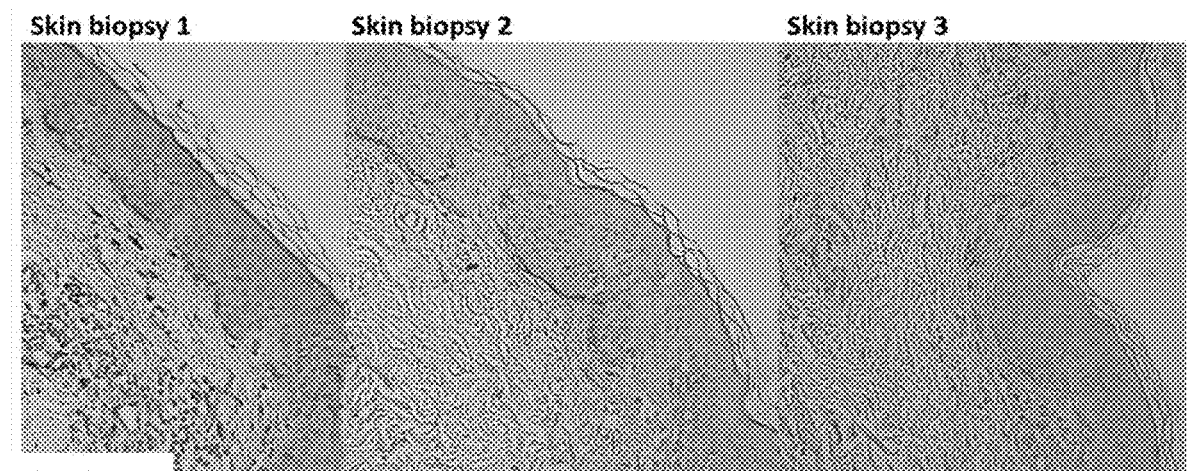

FIG. 8A demonstrates the changes in staining from biopsy 1 obtained in all 3 individuals, 2 years ago, biopsy 2 obtained 6 months ago and biopsy 3 obtained 2 weeks ago post 6 months of NAC therapy. So overall the drug is reducing the intensity of the biomarker (amyloid-cystatin protein aggregate) in the skin, suggesting that amyloid precipitation in other organs is also reduced as previously demonstrated (21).

Based on staining results measuring the amyloid-cystatin protein complex aggregates in the skin, it became evident that the proband who had very high level of amyloid-cystatin stain on the first skin biopsy had not progressed in any significant way (measured by the intensity of the stain) between skin biopsy #1 and #2, whereas her father and her older sibling (both of whom are also carriers of the L68Q mutant) showed significant progression in the intensity of the stain, reflective of increased amyloid complex precipitation in the skin over time in the absence of NAC therapy. It is noteworthy that the proband was on the NAC drug for about 9 months to treat her lungs. She had stopped the therapy only for a few months prior to the second biopsy. Second biopsy was performed first as a baseline to serve as biomarker response to subsequent NAC therapy.

The three biopsies for each individual were stained all together at the same time, for legitimate comparison. The lead proband (stroke×3 in 9 months) has been 100% compliant with NAC therapy of 600 mg 3× per day and she demonstrated highly visible reduction in the amyloid stain in comparison with her original skin biopsy, which amounted to 75% reduction at the end of the 6 months of prospective therapy (FIG. 8A). Her father's reduction in staining amounted to 50% and reduction in staining of her sister's biopsy was less obvious as she had taken lower doses of NAC as indicated in material and methods sections.

Figure 8B:
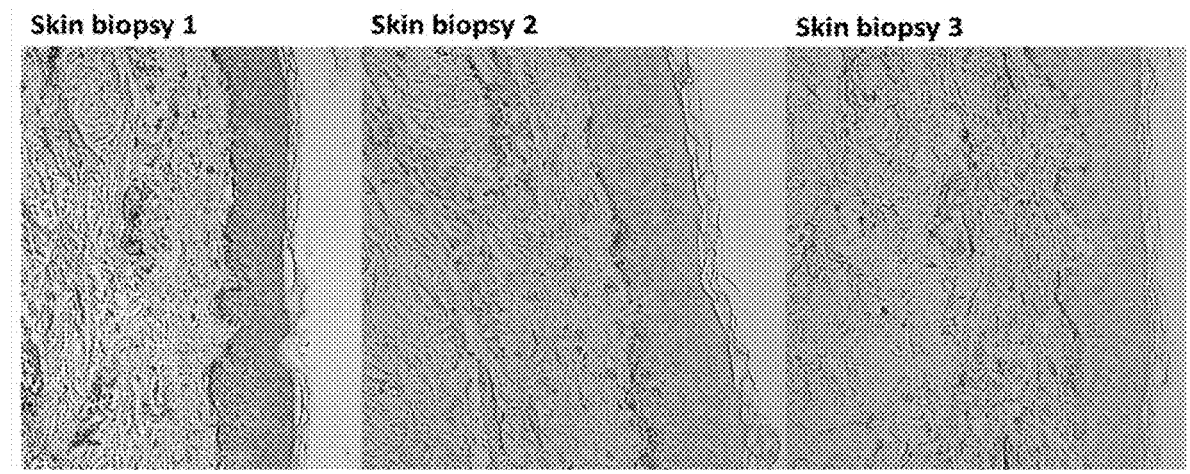

Finally, blood samples were acquired from 7 members of an Icelandic family known to be carriers of the L68Q mutation. Five of the family members were of known mutation status (3 L68Q carriers, 2 wild type), and DNA from all individuals was Sanger sequenced to confirm known statuses and to determine the status of the previously unexamined individuals, one of whom was found to carry the mutation. Mutation status and relationship to the proband in this family are shown in FIG. 8B. Western blotting of plasma run under reducing conditions showed a reduction of the amount of total Cyst-C in adult carriers of the L68Q mutation (proband, sibling, father). The child carrier did not show a reduction in the amount of protein, indicating potential age-related effects (also not on any therapy). Blotting of non-reduced samples showed detection of high molecular weight complexes in the child carrier. In other subjects, interpretation of these results is complicated by the fact that the adult carriers of the mutation are all taking NAC regularly. It is possible that oligomers would be detectable in adult L68Q carriers not taking NAC.

Both NAC derivatives have been proposed to have increased membrane permeability, due to the replacement of a hydroxyl group with less polar substituents. Increased membrane permeability often correlates with better crossing of the blood brain barrier. To access the membrane permeability of the derivative compounds, live cells were treated with NAC or the derivatives. If the compounds cross the cell membrane, we expect to see impacts of the derivatives on accumulation of intracellular oligomers of L68Q Cyst-C. As shown in FIG. 6, the compounds reduced the amount of high molecular weight Cyst-C in the supernatants. The lesser effects on the intracellular material is likely due to a timing issue. The cells continuously produce L68Q Cyst-C at overexpressed levels, and any compound that enters the cells may be consumed quickly, having an earlier effect that is lost with continued culture.

Discussion

Identification of agents with the ability to reduce hCC dimerization and amyloid fibril formation is the key for the development of drugs for the treatment and/or prevention of the amyloid formation and lethal brain hemorrhage associated with HCCAA. The hCC variant is responsible for HCCAA and there is no treatment available to avoid early death by brain hemorrhage. Here, we first created cells that produce and secrete detectable levels of hCC (wt or L68Q) capable of oligomerizing under non-reducing conditions, and we then show that short incubation with either GSH or NAC breaks oligomers into monomers of both intracellular and secreted hCC L68Q. We show that treatment with either NAC or GSH reduces oligomerization of the secreted hCC L68Q at 24, 48 and 72 h and that treatment with NAC in human patients not only prevents ongoing precipitation of amyloid in the skin, but also reduces previously precipitated amyloid in a significant way, with over 75% reduction observed following 6 months of oral therapy with doses that are well tolerated and without adverse events.

The cellular system developed was constructed to identify agents that could reduce the hCC dimerization and amyloid fibril formation "in vivo" of both wt cystatin C and L68Q variant. Previous systems for the study of the dimerization of hCC had been developed, however, most of them were performed mainly with wildtype cystatin C as it is extremely difficult to produce sufficient amounts of monomeric L68Q-cystatin C (14). The genetically engineered HEK-293T cells with the expression of both c-terminal tagged wt and L68Q hCC provide a superior model to study and characterize the impact of the small molecules on both the secreted and the intracellular levels of wt and L68Q hCC. It is important to highlight that the study and characterization of agents that reduce oligomerization should be made on both fractions because the behavior is different; in particular, on the L68Q-hCC variant. This variant was found mainly as LMW oligomers in the intracellular fraction but mainly forms HMW in the extracellular compartment. These can be due to either the secretion process induces oligomerization of the L68Q variant or because the environmental conditions of the extracellular compartment promote the oligomerization of this variant or because the oligomerization prolonges the half-life of the protein.

L68Q cystatin C, is highly amyloidogenic, and subjects carrying the corresponding mutation suffer from massive cerebral amyloidosis leading to brain hemorrhage and death in early adult life (16). Other amyloid diseases such as Alzheimer, Parkinson, and HD have similar amyloid origins and they are also caused by accumulation of misfolded proteins. This broad-spectrum effect of proteotoxic stress has led to the term "proteinopathies" for neurodegenerative diseases. Interestingly, the risk of getting any of these neurodegenerative diseases increases dramatically with age (22), probably, as a consequence of an increase in protein-misfolding stress, a reduced proteasome activity and a decrease in antioxidant defenses that drive to an extracellular accumulation of misfolded proteins (22). The proteasome and autophagy-lysosomal pathways are the major routes for intracellular aggregation clearance. However, little is known about any corresponding mechanisms that operate extracellularly and about effective strategies to slow or prevent the neurodegeneration resulting from these diseases in humans (23).

Glutathione (GSH) is synthesized in the cytosol from the precursor amino acids glutamate, cysteine and glycine and it is considered the primary endogenous antioxidant in the cell. It is present in the cell at different concentrations, which can go up to 10 mM, depending on the subcellular compartment being present at high concentrations on the cytosol and very low concentration inside the ER (24). Protein disulfide bonds rarely form in the cytosol because of the high concentrations of GSH, by contrast, the lumen of the endoplasmic reticulum (ER) and the extracellular compartment contains a relatively higher concentration of oxidized glutathione (GSSG) (25). This differential distribution of GSH allows the formation of native disulfide bonds in the ER through a complex process involving not only disulfide-bond formation, but also the isomerization of non-native disulfide bonds. Our immunofluorescence studies and previous reports indicate that hCC localizes in late-endosomes/prelysosomes, as well as in the Golgi/ER/early-endosomal compartment (20). This localization is in agreement with typical characteristics of a secretory protein and it is consistent with the hypothesis that L68Q hCC polymerizes in these compartments where exposure to GSH is reduced thereby increasing aggregation, thus, explaining the released aggregates in the extracellular compartment.

Under normal conditions, GSH levels are regulated by two major mechanisms: by controlling the rates of its synthesis and of its export from cells; however, GSH levels are also influenced by agents or conditions that alter the thiol redox state that lead to the formation of glutathione S-conjugates or complexes, and/or that disrupt the distribution of GSH among various intracellular organelles. In addition, GSH levels are affected by the nutritional status and hormonal/stress levels, they exhibit developmental and diurnal variations, and are affected by certain physiological states, including pregnancy and exercise (26-33). Physiological levels of GSH in blood should provide an appropriate antioxidant environment that avoids extracellular accumulation of proteins, however, presence of mutations like hCC L68Q or deficiencies in the levels of GSH, as a consequence of nutritional status or age, could drive to undesired accumulation of misfolded proteins (3). In addition, it is known that GSH deficiency, or a decrease in the GSH/glutathione disulfide (GSSG) ratio, manifests itself largely through an increased susceptibility to oxidative stress, and the resulting damage is thought to be involved in diseases such as Parkinson's disease, and Alzheimer's disease and it is strongly associated with other age-related pathologies (34, 35). Results shown in this work indicates that NAC can represent an interesting therapeutic approach to amyloid diseases such as HCCAA, by the reduction of accumulation of amyloid proteins.

Acetylcysteine is a synthetic N-acetyl derivative of the endogenous amino acid L-cysteine, a precursor of the antioxidant enzyme glutathione. Both GSH and NAC already have been approved for use in humans and have been administered at high doses for long periods without adverse side effects. They work as a direct reactive oxygen species (ROS) scavenger and as a source of SH groups, stimulating the GSH synthesis and increasing the presence of 1) non-protein and 2) protein SH groups. Acetylcysteine, in addition, also regenerates liver stores of GSH. These effects confer NAC the ability to reduce disulfide bounds and are the reason why NAC is widely used to reduce viscosity and elasticity of the mucus among other uses. Our data show that treatment with antioxidants such as GSH and NAC (and also DTT or beta-MetOH) abolishes hCC oligomerization. This effect indicates that disulfide bond formation is essential for the oligomerization process. Disulfide bonds do not appear to be directly involved in the dimerization process (16), however the presence of two disulfide bonds in human cystatin C (as in all type 2 cystatins), and the preservation of them in the dimeric structure indicates its key role in the dimerization process (16). We postulate that the intramolecular disulfide bonds are essential for the correct folding of the hCC monomer and for the exchange of three-dimensional 'subdomains' between the two subunits of the dimer and its impairment abolish the oligomerization.

Our data show that treatment with NAC will increase GSH production and both antioxidants will reduce oligomerization of the secreted hCC reducing the amyloid formation on the brain of persons with HCCAA. Treatment with GSH may be effective, however, its low bioavailability limits it's potential as a therapeutic for the treatment of patients with HCCAA. NAC appears as the perfect candidate because of its role in restoring GSH levels, antioxidant properties, and its ability to break disulfide bonds reviewed in (36). In addition, NAC supplementation significantly improved coronary and peripheral vasodilatation (37). Specific to brain disorders, NAC has been administered with some efficacy in patients with Alzheimer disease (38), and our data show that it can be a good alternative for the HCCAA.

Cellular membranes, along with the blood-brain barrier, exhibit reduced permeability to NAC, thus extracellular NAC treatment does not appear to impact the dimerization status of the intracellular levels of L68Q hCC (data not shown). Accordingly, the effects of NAC derivatives including without limitation, N-acetylcysteine ethyl ester (NACET) or N-acetylcysteine methyl ester are preferably administered. These novel lipophilic cell permeable membrane cysteine derivatives should provide good candidates for the oral use as an $H_2S$ producer in the treatment of amyloid disease like HCCAA (39).

The reduction observed in the amyloid stain in the skin biopsies with NAC treatment is highly encouraging and indicates that this therapy will have efficacy in treating patients with HCCAA. As amyloid precipitates in all organs, there is no reason to believe that there is ongoing precipitation and accumulation of amyloid in the brain, when reduction is observed in the skin. More likely, there is similar reduction in other body organs, including brain vessels and the brain. No new events have occurred in any of the 3 individuals, all of whom have continued therapy and the proband is now approximately two years post her third and last stroke.

It is noteworthy that a significant number of the HCCAA patients in Iceland never get a clinical stroke, and only present with dementia at an early age. As the disease process of amyloid precipitation is comparable in HCCAA patients to that in Alzheimer disease, blocking the ability of amyloid fibers to dimerize and polymerize (which is enhanced by the L68Q-cystatin C founder mutation cases), could help Alzheimer patients with amyloid associated dementia. Thus, NAC therapy or NAC-like compounds could be beneficial for Alzheimer disease.

The analogy here is familial combined hypercholesterolemia (FCH), as statin drugs were developed to treat this familial condition (patients with FCH develop stroke and myocardial infarction in their 20s); it subsequently became evident that elevated cholesterol was harmful and a major risk factor for MI and stroke, and that patients with CV risk factors benefitted from statin treatment. HCCAA is an enhanced amyloid precipitation that occurs in early life and leads to catastrophic events in the 20's and early dementia. This process is somewhat comparable but occurs slower in Alzheimer disease so the dementia typically presents not until mid to late 60's or 70's—whereas the treatment would be the same.

REFERENCES

1. Palsdottir, A. et al. Mutation in cystatin C gene causes hereditary brain haemorrhage. *Lancet* 2, 603-604 (1988).
2. Abrahamson, M., Barrett, A. J., Salvesen, G. & Grubb, A. Isolation of six cysteine proteinase inhibitors from human urine. Their physicochemical and enzyme kinetic properties and concentrations in biological fluids. *J Biol Chem* 261, 11282-11289 (1986).
3. Snorradottir, A. O. et al. Deposition of collagen IV and aggrecan in leptomeningeal arteries of hereditary brain haemorrhage with amyloidosis. *Brain Res* 1535, 106-114 (2013).
4. Palsdottir, A. et al. A drastic reduction in the life span of cystatin C L68Q carriers due to life-style changes during the last two centuries. *PLoS Genet* 4, e1000099 (2008).

5. Gudmundsson, G., Hallgrimsson, J., Jonasson, T. A. & Bjarnason, O. Hereditary cerebral haemorrhage with amyloidosis. *Brain* 95, 387-404 (1972).
6. Osk Snorradottir, A. et al. Parenchymal cystatin C focal deposits and glial scar formation around brain arteries in Hereditary Cystatin C Amyloid Angiopathy. *Brain Res* 1622, 149-162 (2015).
7. Abrahamson, M., Grubb, A., Olafsson, I. & Lundwall, A. Molecular cloning and sequence analysis of cDNA coding for the precursor of the human cysteine proteinase inhibitor cystatin C. *FEBS Lett* 216, 229-233 (1987).
8. Grubb, A. & Lofberg, H. Human gamma-trace, a basic microprotein: amino acid sequence and presence in the adenohypophysis. *Proc Natl Acad Sci USA* 79, 3024-3027 (1982).
9. Grubb, A. O. Cystatin C—properties and use as diagnostic marker. *Adv Clin Chem* 35, 63-99 (2000).
10. Henskens, Y. M. et al. Effect of periodontal treatment on the protein composition of whole and parotid saliva. *J Periodontol* 67, 205-212 (1996).
11. Turk, V. & Bode, W. The cystatins: protein inhibitors of cysteine proteinases. *FEBS Lett* 285, 213-219 (1991).
12. Bode, W. et al. The 2.0 A X-ray crystal structure of chicken egg white cystatin and its possible mode of interaction with cysteine proteinases. *EMBO J* 7, 2593-2599 (1988).
13. Orlikowska, M., Jankowska, E., Kolodziejczyk, R., Jaskolski, M. & Szymanska, A. Hinge-loop mutation can be used to control 3D domain swapping and amyloidogenesis of human cystatin C. *J Struct Biol* 173, 406-413 (2011).
14. Kolodziejczyk, R. et al. Crystal structure of human cystatin C stabilized against amyloid formation. *FEBS J* 277, 1726-1737 (2010).
15. Janowski, R. et al. Human cystatin C, an amyloidogenic protein, dimerizes through three-dimensional domain swapping. *Nat Struct Biol* 8, 316-320 (2001).
16. Janowski, R., Abrahamson, M., Grubb, A. & Jaskolski, M. Domain swapping in N-truncated human cystatin C. *J Mol Biol* 341, 151-160 (2004).
17. Janowski, R., Kozak, M., Abrahamson, M., Grubb, A. & Jaskolski, M. 3D domain-swapped human cystatin C with amyloid like intermolecular beta-sheets. *Proteins* 61, 570-578 (2005).
18. Wahlbom, M. et al. Fibrillogenic oligomers of human cystatin C are formed by propagated domain swapping. *J Biol Chem* 282, 18318-18326 (2007).
19. Tsiolaki, P. L., Louros, N. N., Hamodrakas, S. J. & Iconomidou, V. A. Exploring the 'aggregation-prone' core of human Cystatin C: A structural study. *J Struct Biol* 191, 272-280 (2015).
20. Sipe, J. D. et al. Amyloid fibril protein nomenclature: 2012 recommendations from the Nomenclature Committee of the International Society of Amyloidosis. *Amyloid* 19, 167-170 (2012).
21. Palsdottir, A., Snorradottir, A. O. & Thorsteinsson, L. Hereditary cystatin C amyloid angiopathy: genetic, clinical, and pathological aspects. *Brain Pathol* 16, 55-59 (2006).
22. Snorradottir, A. O. et al. Pathological changes in basement membranes and dermal connective tissue of skin from patients with hereditary cystatin C amyloid angiopathy. *Lab Invest* 97, 383-394 (2017).
23. Perlenfein, T. J., Mehlhoff, J. D. & Murphy, R. M. Insights into the mechanism of cystatin C oligomer and amyloid formation and its interaction with beta-amyloid. *J Biol Chem* 292, 11485-11498 (2017).
24. Östner, G. et al. High throughput testing of drug library substances and monoclonal antibodies for capacity to reduce formation of cystatin C dimers to identify candidates for treatment of hereditary cystatin C amyloid angiopathy. *Scandinavian Journal of Clinical and Laboratory Investigation* 71, 676-682 (2011).
25. Chen, J., Armstrong, A. H., Koehler, A. N. & Hecht, M. H. Small molecule microarrays enable the discovery of compounds that bind the Alzheimer's Abeta peptide and reduce its cytotoxicity. *J Am Chem Soc* 132, 17015-17022 (2010).
26. Nilsson, M. et al. Prevention of domain swapping inhibits dimerization and amyloid fibril formation of cystatin C: use of engineered disulfide bridges, antibodies, and carboxymethylpapain to stabilize the monomeric form of cystatin C. *J Biol Chem* 279 (2004).
27. Östner, G. et al. Stabilization, Characterization, and Selective Removal of Cystatin C Amyloid Oligomers. *Journal of Biological Chemistry* 288, 16438-16450 (2013).
28. Pollak, J., Szymanska, A., Lindstrom, V. & Grubb, A. Production of Cystatin C Wild Type and Stabilized Mutants. *EJIFCC* 20, 166-170 (2010).
29. Bjarnadottir, M. et al. Intracellular accumulation of the amyloidogenic L68Q variant of human cystatin C in NIH/3T3 cells. *Mol Pathol* 51, 317-326 (1998).
30. Benedikz, E. et al. Cellular processing of the amyloidogenic cystatin C variant of hereditary cerebral hemorrhage with amyloidosis, Icelandic type. *Amyloid* 6, 172-182 (1999).
31. Thorsteinsson, L. et al. On the role of monocytes/macrophages in the pathogenesis of central nervous system lesions in hereditary cystatin C amyloid angiopathy. *J Neurol Sci* 108, 121-128 (1992).
32. Wei, L. et al. Instability of the amyloidogenic cystatin C variant of hereditary cerebral hemorrhage with amyloidosis, Icelandic type. *J Biol Chem* 273, 11806-11814 (1998).
33. Merz, G. S. et al. Human cystatin C forms an inactive dimer during intracellular trafficking in transfected CHO cells. *J Cell Physiol* 173, 423-432 (1997).
34. Xu, Y., Lindemann, P., Vega-Ramos, J., Zhang, J. G. & Villadangos, J. A. Developmental regulation of synthesis and dimerization of the amyloidogenic protease inhibitor cystatin C in the hematopoietic system. *J Biol Chem* 289, 9730-9740 (2014).
35. Benedikz, E., Blondal, H. & Gudmundsson, G. Skin deposits in hereditary cystatin C amyloidosis. *Virchows Arch A Pathol Anat Histopathol* 417, 325-331 (1990).
36. Unnithan, A. S., Choi, H. J., Titler, A. M., Posimo, J. M. & Leak, R. K. Rescue from a two hit, high-throughput model of neurodegeneration with N-acetyl cysteine. *Neurochem Int* 61, 356-368 (2012).
37. Yerbury, J. J., Stewart, E. M., Wyatt, A. R. & Wilson, M. R. Quality control of protein folding in extracellular space. *EMBO Rep* 6, 1131-1136 (2005).
38. Lai, A. Y. & McLaurin, J. Clearance of amyloid-beta peptides by microglia and macrophages: the issue of what, when and where. *Future Neurol* 7, 165-176 (2012).
39. Go, Y. M. & Jones, D. P. Redox compartmentalization in eukaryotic cells. *Biochim Biophys Acta* 1780, 1273-1290 (2008).
40. Hwang, C., Sinskey, A. J. & Lodish, H. F. Oxidized redox state of glutathione in the endoplasmic reticulum. *Science* 257, 1496-1502 (1992).

41. Lautwein, A. et al. Inflammatory stimuli recruit cathepsin activity to late endosomal compartments in human dendritic cells. *Eur J Immunol* 32, 3348-3357 (2002).
42. DeLeve, L. D. & Kaplowitz, N. Importance and regulation of hepatic glutathione. *Semin Liver Dis* 10, 251-266 (1990).
43. Hahn, R., Wendel, A. & Flohe, L. The fate of extracellular glutathione in the rat. *Biochim Biophys Acta* 539, 324-337 (1978).
44. Isaacs, J. T. & Binkley, F. Cyclic AMP-dependent control of the rat hepatic glutathione disulfide-sulfhydryl ratio. *Biochim Biophys Acta* 498, 29-38 (1977).
45. Kemp, M., Go, Y. M. & Jones, D. P. Nonequilibrium thermodynamics of thiol/disulfide redox systems: a perspective on redox systems biology. *Free radical biology & medicine* 44, 921-937 (2008).
46. Lauterburg, B. H., Smith, C. V., Hughes, H. & Mitchell, J. R. Biliary excretion of glutathione and glutathione disulfide in the rat. Regulation and response to oxidative stress. *J Clin Invest* 73, 124-133 (1984).
47. Meister, A. & Tate, S. S. Glutathione and related gamma-glutamyl compounds: biosynthesis and utilization. *Annu Rev Biochem* 45, 559-604 (1976).
48. Meister, A. & Anderson, M. E. Glutathione. *Annu Rev Biochem* 52, 711-760 (1983).
49. Uhlig, S. & Wendel, A. The physiological consequences of glutathione variations. *Life Sci* 51, 1083-1094 (1992).
50. Ballatori, N. et al. Glutathione dysregulation and the etiology and progression of human diseases. *Biol Chem* 390, 191-214 (2009).
51. Samiec, P. S. et al. Glutathione in human plasma: decline in association with aging, age-related macular degeneration, and diabetes. *Free radical biology & medicine* 24, 699-704 (1998).
52. Atkuri, K. R., Mantovani, J. J., Herzenberg, L. A. & Herzenberg, L. A. N-Acetylcysteine—a safe antidote for cysteine/glutathione deficiency. *Curr Opin Pharmacol* 7, 355-359 (2007).
53. Aitio, M. L. N-acetylcysteine—passe-partout or much ado about nothing? *Br J Clin Pharmacol* 61, 5-15 (2006).
54. Bavarsad Shahripour, R., Harrigan, M. R. & Alexandrov, A. V. N-acetylcysteine (NAC) in neurological disorders: mechanisms of action and therapeutic opportunities. *Brain Behav* 4, 108-122 (2014).
55. Andrews, N. P., Prasad, A. & Quyyumi, A. A. N-acetylcysteine improves coronary and peripheral vascular function. *J Am Coll Cardiol* 37, 117-123 (2001).
56. Adair, J. C., Knoefel, J. E. & Morgan, N. Controlled trial of N-acetylcysteine for patients with probable Alzheimer's disease. *Neurology* 57, 1515-1517 (2001).
57. Giustarini, D., Milzani, A., Dalle-Donne, I., Tsikas, D. & Rossi, R. N-Acetylcysteine ethyl ester (NACET): A novel lipophilic cell-permeable cysteine derivative with an unusual pharmacokinetic feature and remarkable antioxidant potential. *Biochemical pharmacology* 84, 1522-1533 (2012).
58. Cohen, G. B. et al. The selective downregulation of class I major histocompatibility complex proteins by HIV-1 protects HIV-infected cells from NK cells. *Immunity* 10, 661-671 (1999).
59. Schindelin, J. et al. Fiji: an open-source platform for biological-image analysis. *Nat Methods* 9, 676-682 (2012).

While certain of the preferred embodiments of the present invention have been described and specifically exemplified above, it is not intended that the invention be limited to such embodiments. It will be apparent to one skilled in the art that various changes and modifications can be made therein without departing from the scope of the present invention, as set forth in the following claims.

---

What is claimed is:

1. A method for treating hereditary cystatin C amyloid angiopathy (HCCAA) comprising delivering an effective amount of at least one antioxidant to a patient at risk for HCCAA, or having HCCAA, said antioxidant being effective to reduce amyloid-cystatin protein misfolding, thereby alleviating symptoms of said HCCAA.

2. The method of claim 1, wherein said hereditary cystatin C amyloid angiopathy (HCCAA) is caused by mutated cystatin C and said treatment reduces amyloid-cystatin oligomerization.

3. The method of claim 2, wherein said mutated cystatin C comprises a L68Q cystatin C.

4. The method of claim 1, wherein said antioxidant is selected from the group consisting of glutathione, N-acetyl cysteine, NAC-amide, NAC-ethyl ester, and Zinc mercaptide N-acetyl cysteine carboxylate salt.

5. The method of claim 1, further comprising performing a skin biopsy on said subject following treatment to assess reduction in amyloid-cystatin protein aggregates in skin.

6. The method of claim 1, further comprising administration of an ionophore.

7. The method of claim 1, further comprising administration of an anti-inflammatory agent.

8. The method of claim 7, wherein said antioxidant is a NAC derivative selected from NAC-amide, NAC-ethyl ester and zinc mercaptide N-acetyl cysteine carboxylate salt and said anti-inflammatory agent is selected from the group consisting of one or more of corticosteroids, aspirin, celecoxib, diclofenac, diflunisal, etodolac, ibuprofen, indomethacin, ketoprofen, ketorolac, nabumetone, naproxen, oxaprozin, piroxicam, salsalate, sulindac, tolmetin, interleukin (IL)-1 receptor antagonist, IL-4, IL-6, IL-10, IL-11, IL-13, cytokine receptors for IL-1, tumor necrosis factor-alpha, and IL-18.

9. The method of claim 1, further comprising administration of one or more of monensin, papain, cathepsin B, and falcipain.

* * * * *

SEQUENCE LISTING

```
<160> NUMBER OF SEQ ID NOS: 4

<210> SEQ ID NO 1
<211> LENGTH: 35
<212> TYPE: DNA
<213> ORGANISM: Artificial Sequence
<220> FEATURE:
<223> OTHER INFORMATION: Primer

<400> SEQUENCE: 1
gatcgaattc gccaccatgg ccgggcccct gcgcg                                35

<210> SEQ ID NO 2
<211> LENGTH: 66
<212> TYPE: DNA
<213> ORGANISM: Artificial Sequence
<220> FEATURE:
<223> OTHER INFORMATION: Primer

<400> SEQUENCE: 2
tcgcggccgc ctacagatcc tcttctgaga tgagtttttg ttcggcgtcc tgacaggtgg      60
atttcg                                                                66

<210> SEQ ID NO 3
<211> LENGTH: 45
<212> TYPE: DNA
<213> ORGANISM: Artificial Sequence
```

```
<220> FEATURE:
<223> OTHER INFORMATION: Primer

<400> SEQUENCE: 3
gtgaactact tcttggacgt cgagcagggc cgaaccacgt gtacc            45

<210> SEQ ID NO 4
<211> LENGTH: 45
<212> TYPE: DNA
<213> ORGANISM: Artificial Sequence
<220> FEATURE:
<223> OTHER INFORMATION: Primer

<400> SEQUENCE: 4
ggtacacgtg gttcggccct gctcgacgtc caagaagtag ttcac            45
```